(12) United States Patent
Zhang

(10) Patent No.: US 11,106,056 B2
(45) Date of Patent: Aug. 31, 2021

(54) SUBZONAL MULTIFOCAL DIFFRACTIVE LENS

(71) Applicant: Aizhong Zhang, Rochester, NY (US)

(72) Inventor: Aizhong Zhang, Rochester, NY (US)

( * ) Notice: Subject to any disclaimer, the term of this patent is extended or adjusted under 35 U.S.C. 154(b) by 179 days.

(21) Appl. No.: 16/368,826

(22) Filed: Mar. 28, 2019

(65) Prior Publication Data

US 2020/0310159 A1    Oct. 1, 2020

(51) Int. Cl.
*G02C 7/04* (2006.01)
*A61F 2/16* (2006.01)

(52) U.S. Cl.
CPC ............ *G02C 7/044* (2013.01); *A61F 2/1618* (2013.01); *A61F 2/1656* (2013.01); *G02C 2202/20* (2013.01)

(58) Field of Classification Search
CPC ........ G02C 7/00; G02C 7/02; G02C 2202/16; G02C 2202/12; G02C 2202/10; G02C 2202/20
See application file for complete search history.

(56) References Cited

U.S. PATENT DOCUMENTS

| | | |
|---|---|---|
| 4,210,391 A | 7/1980 | Cohen |
| 4,338,005 A | 7/1982 | Cohen |
| 4,340,283 A | 7/1982 | Cohen |
| 4,637,697 A | 1/1987 | Freeman |
| 4,641,934 A | 2/1987 | Freeman |
| 4,642,112 A | 2/1987 | Freeman |
| 4,655,565 A | 4/1987 | Freeman |
| 4,830,481 A | 5/1989 | Futhey et al. |
| 4,936,666 A | 6/1990 | Futhey et al. |
| 4,995,715 A | 2/1991 | Cohen |
| 5,016,977 A | 5/1991 | Baude et al. |
| 5,017,000 A | 5/1991 | Cohen |
| 5,054,905 A | 10/1991 | Cohen |
| 5,056,908 A | 10/1991 | Cohen |
| 5,104,212 A | 4/1992 | Taboury et al. |
| 5,116,111 A | 5/1992 | Simpson et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,129,718 A | 7/1992 | Futhey et al. |
| 5,144,483 A | 9/1992 | Cohen |
| 5,229,797 A | 7/1993 | Futhey et al. |

(Continued)

OTHER PUBLICATIONS

Buralli, Dale A., G. Michael Morris, and John R. Rogers. "Optical performance of holographic kinoforms." Applied optics 28, No. 5 (1989): 976-983.

(Continued)

*Primary Examiner* — Robert E. Tallman
(74) *Attorney, Agent, or Firm* — Lynne M. Blank, Esq.

(57) ABSTRACT

The apparatus and design method of a subzonal multifocal diffractive (SMUD) lens is described herein. The apparatus includes a plurality of annular concentric zones. Each zone are further divided into at least two subzones, where the division of the subzones is arbitrary, but the division is consistent with respect to radius squared $r^2$ across all zones. The subzone phase profile is independent with each other within the same zone, and can be optimized to achieve a desired splitting ratio among all foci.

19 Claims, 20 Drawing Sheets

(56) References Cited

U.S. PATENT DOCUMENTS

| | | | |
|---|---|---|---|
| 5,296,881 | A | 3/1994 | Freeman |
| 5,652,638 | A | 7/1997 | Roffman et al. |
| 5,699,142 | A | 12/1997 | Lee et al. |
| 5,748,282 | A | 5/1998 | Freeman |
| 6,536,899 | B1 | 3/2003 | Fiala |
| 8,500,805 | B2 | 8/2013 | Kobayashi et al. |
| 9,320,594 | B2 | 4/2016 | Schwiegerling |
| 2014/0172088 | A1 | 6/2014 | Carson et al. |
| 2018/0263760 | A1* | 9/2018 | Canovas Vidal ..... A61F 2/1645 |
| 2018/0373060 | A1* | 12/2018 | Knox .................. A61F 2/14 |
| 2019/0041664 | A1* | 2/2019 | Ando .................. A61F 2/1654 |

OTHER PUBLICATIONS

Faklis, Dean, and G. Michael Morris. "Spectral properties of multiorder diffractive lenses." Applied Optics 34, No. 14 (1995): 2462-2468.

Davison, James A., and Michael J. Simpson "History and development of the apodized diffractive intraocular lens." Journal of Cataract & Refractive Surgery 32, No. 5 (2006): 8.

\* cited by examiner

Prior Art

Prior Art

SUBZONAL MULTIFOCAL DIFFRACTIVE LENS

FIELD OF THE INVENTION

This invention relates to the field of diffractive optics, in particular, it relates to multifocal diffractive lenses in ophthalmology in the form of intraocular lenses, contact lenses and intracorneal lenses, etc, to treat presbyopia or cataracts.

BACKGROUND OF THE INVENTION

The human lens inside the eye naturally ages, and after the age of forty, people gradually lose the capability to accommodate to focus on nearby objects by changing the shape of the lens and the lens capsule with the ciliary muscles. Although not directly an accommodating lens, a multifocal contact lens or intraocular lens could enable the patients to focus at both distant and nearby objects, and even at some intermediate distances.

Further, a cataract, i.e. a clouding lens, could develop in some patients with aging or other related health and environmental factors, such as diabetes, overexposure to ultraviolet (UV) radiation, etc. Clinically, the cataract lens is removed by the process of phacoemulsification, and an artificial intraocular lens is inserted to replace the clouded natural lens. A multifocal intraocular lens could help the patients to recover vision without the need of a spectacle to compensate for the loss of accommodation after a cataract surgery.

Multifocal diffractive lenses are also used in the form of contact lenses and intracorneal lenses to help patients with presbyopia and other ocular health problems.

Diffractive lenses have been used in ophthalmology for several decades. Conventional diffractive lenses are segmented into zones of equal areas, which are usually referred to as Fresnel zones. Sharp edges are formed at the zone boundaries to create desired optical path differences immediately across zone boundaries to achieve desired diffraction output. The location of zone boundaries determines the focal points positions of the diffractive element, while the optical profile within each zone determines the energy distribution among different focal points of the diffractive element.

Multiple designs of a diffractive surface with Fresnel zones of equal areas have been described in the prior art. A lot of early diffractive lenses used in general optical systems were monofocal lenses to reduce the total system length and weight, while maintaining or improving the optical performance of a conventional system. Since introduced to the field of ophthalmology, early multifocal diffractive lenses were mostly bifocal lenses, which are still used nowadays. In the classical bifocal design, the step height was chosen so that the optical path difference across zone boundaries is $0.5\lambda_0$, where $\lambda_0$ is the design wavelength of the diffractive element. In this way, the energy is equally split between the zeroth order and the first order, with each order containing about 40.53% of the total incident energy, and the rest ~19% energy distributed among higher orders. The step height can be further manipulated to generate desired energy distribution among all the foci. With these bifocal lenses, clear images of both near and far objects are achieved.

Trifocal multifocal diffractive lenses have been further developed to provide sharp images at another intermediate object distance. For example, people with a trifocal diffractive lens implanted to replace the natural crystalline lens could focus sharply at near objects for reading, at distant objects for driving and at an intermediate distance for cooking and computer usage. One classical trifocal diffractive lens design is created by alternating the step height of odd-numbered zones and even-numbered zones.

Early description of the multifocal diffractive lenses in the prior art were developed by Cohen and Freeman. The Cohen patents include U.S. Pat. Nos. 4,210,391; 4,338,005; 4,340,283; 4,995,715; 5,017,000; 5,054,905; 5,056,908; 5,117,306; 5,120,120; 5,121,979; 5,121,980; and 5,144,483. The Freeman patents include U.S. Pat. Nos. 4,641,934; 4,642,112; 4,637,697; 4,655,565; 5,296,881 and 5,748,282. More patents on diffractive lenses include U.S. Pat. Nos. 4,830,481; 4,936,666; 5,129,718; 5,229,797 to Futhey, et al. U.S. Pat. No. 5,104,212 to Taboury et al, U.S. Pat. No. 5,152,788 to Isaacson et al, U.S. Pat. No. 5,116,111 to Simpson et al, U.S. Pat. No. 8,500,805 to Kobayashi et al, U.S. Pat. No. 9,320,594 to Schwiegerling, etc.

In order to emphasize distant vision over near vision in mesopic condition, and to reduce glares and halos in dim conditions, such as night time driving, apodization in diffraction efficiency was introduced in the prior art. The original apodization factor proposed by Lee and Simpson in U.S. Pat. No. 5,699,142 has the form of $$f_{apodize} = 1 - \left(\frac{r - r_{in}}{r_{out} - r_{in}}\right)^e, r_{in} \leq r < r_{out} \quad (1)$$

where $f_{apodize}$ is the apodization factor, and $r_{in}$ and $r_{out}$ are the inner and outer boundaries of the apodization region. e is an exponent.

To correct ophthalmic astigmatism, where there are different optical powers in different meridians, U.S. Pat. No. 5,016,977 teaches a diffractive lenses with hyperbolic or elliptical outlines to generate cylinder power. However, the cylinder power changes with different diffraction orders, while in ophthalmology, the added astigmatism is usually used to correct a fixed residual astigmatism in other parts of the eye, for example, the added astigmatism of an intraocular lens is usually chosen to cancel the corneal astigmatism. Multifocal diffractive lenses with hyperbolic or elliptical astigmatism-correction outlines can only correct residual astigmatism for one order and will introduce additional astigmatism for all the other orders, hence such lenses are only useful for monofocal lenses. Furthermore, when the incident beam is converging or diverging, and when the diffractive substrate surface is curved, additional phase in the transmission function might further lower the image contrast, even for a monofocal diffractive lens. Therefore, this type of design is not commonly used in ophthalmology.

U.S. Pat. No. 5,652,638 teaches a lens combining a toric surface on one side, and a multifocal diffractive surface on the other side. This lens can be used to combine different diffractive orders with a fixed cylinder power to correct ophthalmic astigmatism.

However, one of the main drawbacks of these aforementioned multifocal diffractive lenses is that the lens is segmented into Fresnel zones of substantially equal areas, and the design freedom of independent parameters is limited.

U.S. Pat. No. 6,536,899 to Fiala describes a multifocal lens with subzones. However, in that patent, each of the annular zones is subdivided into at least two subzones, a main subzone and a phase subzone, with the main subzones exhibiting refractive powers such that the combination of the main subzones forms a diffractive lens with at least two principal powers and the phase subzones exhibit other refractive powers such that the average refractive power of each annular zone is substantially equal to at least one of the principal powers. This design type was able to avoid sharp step heights at zone boundaries, but the additional requirement of the refractive powers between adjacent subzones have to be satisfied.

U.S. Pat. Application No. 2014/0172088 describes an intraocular lens with a plurality of zones, and each zone has a plurality of echelettes. However, the radius of curvature values of all the echelettes within the same zone are the same.

In this invention, a new type of diffractive lens, the subzonal multifocal diffractive (SMUD) lens is described. Within each Fresnel zone, the phase profiles of all subzones are independent to each other.

SUMMARY OF THE INVENTION

It is an object of this invention to provide a multifocal diffractive lens which segments each Fresnel zone into at least two subzones, in order to provide more design freedom to generate desired energy allocation among selected two or more foci.

It is another object of this invention to create a diffractive lens, wherein the division of the subzone within each Fresnel zone is arbitrary, as long as the division is consistent with respect to radius squared $r^2$ among all Fresnel zones in a diffractive lens. Therefore, the projected area of each subzone can be arbitrary, and not necessarily equal to the projected areas of other subzones within the same zone.

It is another object of this invention to provide a diffractive lens that the phase profile of each subzone, which could be a thickness profile or a refractive index profile, is completely independent of that of any other subzone within a Fresnel zone, which will provide more design freedom to achieve desired optical output.

It is also another object of this invention to introduce a phase step factor to characterize the phase profile of each subzone.

It is further another object of this invention to introduce a Fresnel zone spacing factor to adjust the Fresnel zone boundaries to take into account the incidence of a converging or diverging beam and the curvature of the substrate.

It is still another object of this invention to demonstrate a design procedure of subzonal multifocal diffractive lens with analytical and numerical methods.

Other objects and advantages of the invention will become apparent from the following description and the associated drawings.

The subzonal multifocal diffractive lens in this invention comprises a lens having a first surface, which is a subzonal multifocal diffractive surface, and at least a portion of the diffractive surface has a plurality of concentric annular zones from the center to the periphery along radius r, and each zone has a projected area in a plane perpendicular to the optical axis, and the projected areas of all zones are of substantially equal area. Each zone is divided into at least two subzones with one or more division ratios within each zone. Each subzone has a phase profile and a projected area, and the division ratios are the same across all zones so that a repetitive pattern is formed with respect to radius squared $r^2$. The phase profile of each subzone is independent of all other subzones within the same zone, and a phase step is formed at the edge of each subzone. The projected area of each subzone is independent with that of any other subzone within the same zone. The phase profile is a thickness profile or a refractive index profile, which changes with radius r from an inner edge to an outer edge of each subzone. A second surface of the lens is a refractive surface which is optionally of a toric shape with a cylinder power to correct ophthalmic astigmatism.

DETAILED DESCRIPTION OF THE INVENTION

Figure 1:
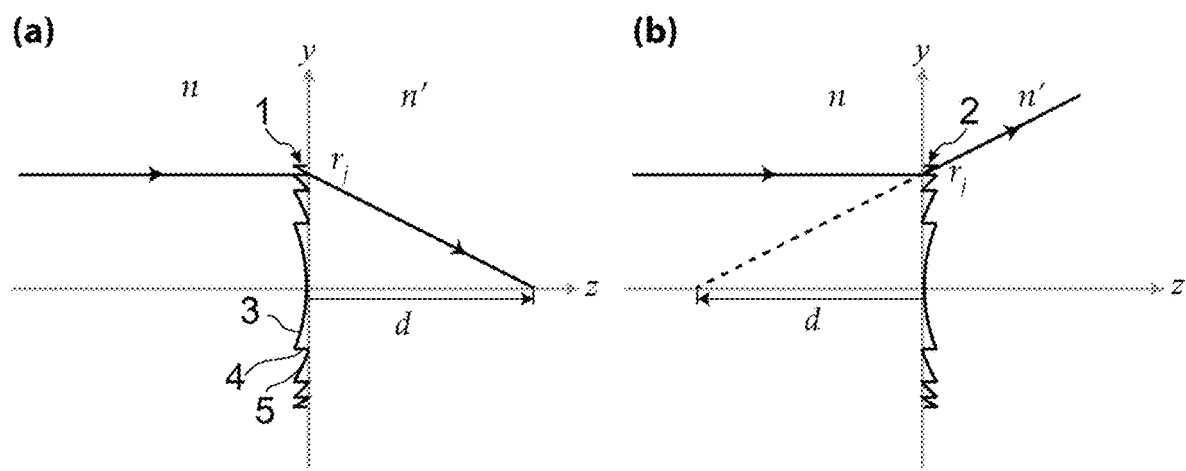
FIG. 1 presents the Fresnel zone boundary determination in the prior art of a diffractive surface on a flat substrate with plane wave incidence. (a) is for a diffractive surface with a positive power (d>0) and (b) is for a diffractive surface with a negative power (d<0).

A diffractive surface with Fresnel zones of equal areas on a flat substrate with plane wave illumination has been analyzed in the prior art. In FIG. 1, a cross-sectional view of a diffractive surface 1 of a diffractive lens is presented, and the lens material of refractive index n is to the left of the diffractive surface and the ambient environment of refractive index n' is to its right. The optical axis is along the z-axis, and the x-y plane is perpendicular to the optical axis. The x-y-z axes form a three-dimensional Cartesian coordinates. The cross-sectional y-z plane is shown in FIG. 1, and the x-axis is perpendicular to y-z plane, though not shown in FIG. 1. The origin of the coordinates system is chosen to be the point where the lens vertex intersects with the optical axis. The diffractive surface comprises a central circular zone 3, a thickness step 4 at the edge of the central zone 3 and an adjacent concentric annular zone 5. $r_j$ is the radius, or semi-aperture, of the edge of the j-th zone of the Fresnel full-period zones, and the radius $r_j$ is measured in a plane perpendicular to the optical axis, such as the x-y plane. $\lambda_0$ is the design wavelength, from which the diffractive profile is defined, and d is the first-order focal length of the diffractive lens. FIG. 1(a) presents a diffractive surface 1 with a positive power (d>0), and FIG. 1(b) presents a diffractive surface 2 with a negative power (d<0).

Referring to FIG. 1(a), the optical path length (OPL) of the ray passing through the edge of the j-th zone and that of the ray along the optical axis through the origin differ by an integer j multiplied by the design wavelength.

$$n'(\sqrt{d^2+r_j^2}-d)=j\lambda_0 \quad (2)$$

When $d \gg \lambda_0$, Eq.(2) is simplified as $$r_j^2=2j\lambda_0 d/n'=2j\lambda_0 d' \quad (3)$$

where $$d'=d/n'(\lambda_0), d'>0 \quad (4)$$

Referring to FIG. 1(b), the OPL equation of the ray passing through the edge of the j-th zone satisfies $$n'(\sqrt{d^2+r_j^2}+d)=j\lambda_0 \quad (5)$$

Similarly, when $d \gg \lambda_0$, Eq.(5) is simplified as $$r_j^2=-2j\lambda_0 d/n'=2j\lambda_0 d' \quad (6)$$

where $$d'=-d/n'(\lambda_0), d'<0 \quad (7)$$

Apparently, d'=|d|, when the ambient environment is air. However, in ophthalmic applications, the ambient environment is usually not air, but aqueous humor, tear film or other body fluids.

Note that for a diffractive surface with a positive power, the OPL is longer for the ray passing through the j-th zone edge, compared with the ray passing along the optical axis through the origin, while for a diffractive surface with negative power, the OPL is shorter when passing through the j-th zone edge.

Using the notation of d', the same formula for $r_j^2$ is obtained for both positive and negative diffractive surfaces. The diffractive lens Fresnel zone boundaries are found to be periodic in $\rho=r^2$. These boundaries segment the diffractive surface into a central circular zone and surrounding concentric annular zones of substantially equal areas.

To maximize the optical energy at the desired focal point(s), constructive interference from different zones is preferred, and this demands not only the zone boundaries, but also the diffractive lens profile to be periodic in $\rho$-space. The transmission function of a diffractive optical surface with rotational symmetry can be expressed as $$t(\rho)=A(\rho)e^{i\phi(\rho)}=A(\rho)e^{ik(\lambda)[n(\lambda)-n'(\lambda)]\delta(\rho)} \quad (8)$$

where $A(\rho)$ is the electric field absorption coefficient, $k=2\pi/\lambda$ is the wavenumber, $n(\lambda)$ is the refractive index of the lens material, $n'(\lambda)$ is the refractive index of the ambient environment. $\delta(\rho)$ is the lens thickness profile. In most ophthalmic lenses, maximum optical throughput is desired, and a transparent diffractive lens with no absorption is preferred. Therefore, without losing generality, $A(\rho)=1$ is assumed in the following analysis. Those skilled in the art can readily extend similar analysis procedures to designs with absorption, i.e. $A(\rho)<1$.

Since the transmission function $t(\rho)$ is a periodic function of $\rho$, it can be expanded into a Fourier series $$t(\rho) = e^{i\phi(\rho)} = e^{ik(\lambda)[n(\lambda)-n'(\lambda)]\delta(\rho)} = \sum_{m=-\infty}^{+\infty} c_m e^{-\frac{i2\pi m\rho}{L}}$$

$$= \sum_{m=-\infty}^{+\infty} c_m e^{-\frac{i\pi m\rho}{\lambda_0 d'}} \quad (9)$$

where $L=2\lambda_0 d'$ is the period in $\rho$, from Eq.(3) and Eq.(6). The coefficients $c_m$ can be obtained from $$c_m = \frac{1}{L}\int_0^L t(\rho)e^{\frac{i2\pi m\rho}{L}}d\rho = \frac{1}{2\lambda_0 d'}\int_0^{2\lambda_0 d'} e^{ik(n-n')\delta(\rho)+\frac{i\pi m\rho}{\lambda_0 d'}}d\rho \quad (10)$$

Apparently, $c_m$ is directly related to the wavelength in use $\lambda$ (implicitly contained in $k=2\pi/\lambda$), refractive indices of the lens material n and the ambient environment n', and the thickness profile $\delta(\rho)$.

The m-th order diffraction efficiency, i.e. the percentage of optical energy transmitted into the m-th order is $$\eta_m = c_m c_m^* \quad (11)$$

The phase transmission of a thin lens with paraxial approximation $$t_{lens} = e^{-\frac{i\pi n'(\lambda)r^2}{\lambda f}} = e^{-\frac{i\pi n'(\lambda)\rho}{\lambda f}} \quad (12)$$

Compare Eq.(9) with Eq.(12), it's clear that the Fourier series represents a series of converging and diverging beams. Each term corresponds to a thin lens with a focal length of $$f_m = \frac{\lambda_0 |d| n'(\lambda)}{\lambda m n'(\lambda_0)} \quad (13)$$

Hence |d| s the first order (m=1) focal length at the design wavelength $\lambda_0$. Further, the optical power is $$\Phi_m = \frac{1}{f_m} = \frac{\lambda m n'(\lambda_0)}{\lambda_0 |d| n'(\lambda)} \quad (14)$$

i.e. the optical power is directly proportional to the wavelength $\lambda$ at a given order m.

Eq.(3) and Eq.(13) demonstrate that the focal points locations are determined by the boundaries positions in a diffractive lens. Eq.(10) and Eq.(11) further show that the diffraction efficiency, i.e. the output energy allocation among all focal points is completely determined by the lens structure within one period.

The mathematical analysis above has been described in the prior art in similar forms. In the following, a novel and generalized mathematical framework to summarize multifocal diffractive lenses designs is introduced to facilitate the description of this invention of a subzonal multifocal diffractive (SMUD) lens.

The diffractive lens profile $\delta(\rho)$ can be any periodic structure of $\rho$. The simplest profile is periodically linear in $\rho$, and hence quadratic in r, and will be analyzed first. More generalized profiles with nonlinear dependence in $\rho$ will be analyzed afterwards. In this invention, a generalized form of the phase profile of multifocal diffractive lenses that are periodically linear in $\rho$ is expressed as $$\phi(\rho; \lambda) = k(\lambda)[n(\lambda) - n'(\lambda)]\delta_0\left(j - \frac{\rho}{2\lambda_0 d'}\right) = 2\pi\alpha\beta\left(j - \frac{\rho}{2\lambda_0 d'}\right) \quad (15)$$

$\rho_j \leq \rho < \rho_{j+1}, \rho_j = 2j\lambda_0 d'$ where $\delta_0$ is the step height, i.e. the thickness difference at the zone boundaries. $\alpha$ is a parameter first introduced by Dammann, which is the wavelength detuning factor to account for the optical path difference for wavelengths other than the design wavelength. Mathematically, $$\alpha = \frac{\phi(\lambda)}{\phi(\lambda_0)} = \frac{\lambda_0[n(\lambda) - n'(\lambda)]}{\lambda[n(\lambda_0) - n'(\lambda_0)]} \quad (16)$$

when $\alpha=1$, $\lambda=\lambda_0$, Eq.(15) is reduced to a monochromatic design.

The parameter $\beta$ is defined as $$\beta = [n(\lambda_0) - n'(\lambda_0)]\delta_0/\lambda_0 \quad (17),$$

and $\beta$ is referred to as a phase step factor, since $2\pi\beta = k(n-n')\delta_0$ is the phase step immediately across the zone boundaries at the design wavelength $\lambda_0$. $\beta > 0$ corresponds to a positive lens, and $\beta < 0$ corresponds to a negative lens.

It is important to point out that the wavelength detuning factor $\alpha$ is determined by the wavelength in use and the refractive indices of the lens material and the ambient environment. $\alpha$ is independent of the lens thickness profile. Once an application is determined, $\alpha$ is usually set to a specific number or limited to a narrow range.

In contrast, the phase step factor $\beta$ is directly related to the lens profile, and $\beta$ is independent of the wavelength in use. Hence, it's the deliberate choice of $\beta$, i.e. the choice of the thickness profile and refractive index profile that characterizes a certain diffractive lens design.

Based on Eq.(10) and Eq.(15):

$$c_m = \frac{1}{2\lambda_0 d'} \int_0^{2\lambda_0 d'} e^{-i\frac{2\pi\alpha\beta\rho}{2\lambda_0 d'} + i\frac{\pi m \rho}{\lambda_0 d'}} d\rho = e^{i\pi(m-\alpha\beta)}\text{sinc}(m - \alpha\beta) \quad (18)$$

where $\text{sinc}(x) = \sin(\pi x)/(\pi x)$.

From Eq.(11), the diffraction efficiency $$\eta_m = c_m c^*_m = \text{sinc}^2(m - \alpha\beta) \quad (19)$$

Without losing generality, the diffractive lens performance at the design wavelength $\lambda_0$, i.e. of the cases with $\alpha=1$, is first analyzed in the following. Different design forms are explored by manipulating the phase step factor $\beta$.

When $\beta=1$, Eq.(15) is reduced to the classical kinoform design, which is a monofocal diffractive lens at the design wavelength $\lambda_0$ with a focal length of d.

Figure 2:
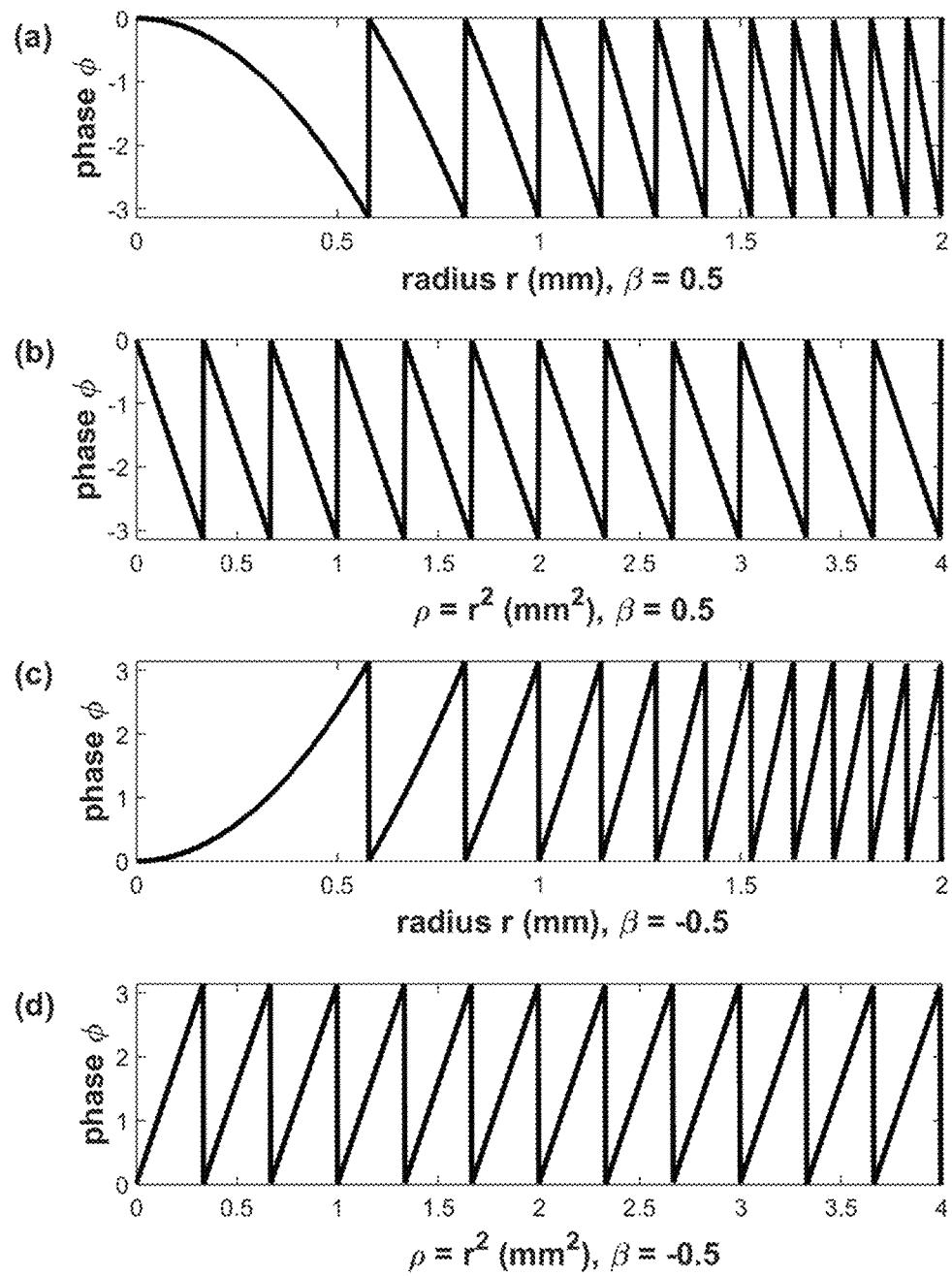
FIG. 2 presents phase profiles in the prior art of two bifocal lenses with regard to radius r and $\rho=r^2$. (a) and (b) are of a positive bifocal lens (d'=300 mm, $\beta=0.5$), while (c) and (d) are of a negative bifocal lens (d'=−300 mm, $\beta=−0.5$). The phase profiles are periodically linear in $\rho$. The design wavelength $\lambda_0$=555 nm for both lenses.

When $\beta=0.5$, Eq.(15) is reduced to a bifocal lens. At the design wavelength $\lambda_0$, the zeroth order and the first order each has a diffraction efficiency of $(2/\pi)^2 \approx 40.53\%$, and the rest ~19% energy is distributed among higher orders. Similarly, $\beta=-0.5$ corresponds to a negative bifocal lens, with ~40.53% of energy in each main focus. FIG. 2 presents phase profiles of two bifocal lenses with respect to radius r and $\rho=r^2$. (a) and (b) are of a positive bifocal lens (d'=300 mm, $\beta=0.5$), while (c) and (d) are of a negative bifocal lens (d'=−300 mm, $\beta=-0.5$). The phase profiles are periodically linear in $\rho$. The design wavelength $\lambda_0$=555 nm for both lenses.

When $\beta=p$, where p is an integer, Eq.(15) is reduced to a multiorder diffractive (MOD) lens or a higher-order diffractive lens, as described by Dean Faklis and G. Michael Morris in "Spectral properties of multiorder diffractive lenses." Applied Optics 34, no. 14 (1995): 2462-2468. Let $d=p F_0$, this MOD lens is monofocal with a focal length of $F_0$ at the design wavelength $\lambda_0$. The monofocality of the MOD lens is clearly shown in FIG. 3, when $\beta$ equals an integer p=1, 2, 3, the corresponding diffraction efficiency of the p-th order becomes unity at $\lambda_0$. This MOD lens is essentially designed with a first-order focal length of $d=p F_0$, while the integer phase step factor $\beta=p$ ensures 100% diffraction efficiency (under scalar diffraction theory) at the p-th order focal point with a focal length of $d/p=F_0$.

As $|\beta|$ gets larger, the step height at the zone boundary increases, the shadowing effect will decrease the diffraction efficiency. On the other hand, because of the quadratic dependence on the radius r of the zone boundaries, the spacing between adjacent zone boundaries gets very close at the rim of the diffractive lens, which poses a challenge for fabrication. In order to increase the manufacturability of the diffractive lens, MOD lens designs with $\beta=p$ are sometimes used at the periphery part of the lens to increase the zone spacing and the step height, with increasing p toward the periphery, while maintaining the same focal length. These periphery region with increasing integer $\beta=p$ is referred to as "superzone" by Futhey in U.S. Pat. No. 4,936,666.

In a lot of applications, monochromatic diffractive lens design ($\alpha=1$) is not enough, and designs of controlled chromatic aberration with a relatively large wavelength bandwidth are preferred. In ophthalmology, diffractive lenses are usually designed in the visible spectrum of about 400 nm to 700 nm. Generally speaking, the wavelength bandwidth around the diffraction efficiency peaks gets smaller with increasing orders. Hence, lower orders are usually used for broadband diffractive lens designs. For a monofocal lens, the first order is usually used. For a bifocal lens, the zeroth order and the first order are usually used. For a trifocal design, the zeroth, first and second orders are usually used. A similar trend holds for multifocal diffractive lenses with more foci.

Even though the generalized form Eq.(15) is able to summarize many different types of multifocal diffractive lenses, it unnecessarily requires a constant phase step factor $\beta$ within each zone.

In this invention, a novel design of a multifocal diffractive lens with two or more segmented subzones within each Fresnel zone is proposed, and each subzone has a phase profile independent of other subzones. A phase step is formed at the edge of each subzone. Each Fresnel zone is divided by one or more concentric division rings with one or more division ratios into at least two subzones. Yet the division ratios are the same with respect to radius squared $r^2$, so that a repetitive pattern is formed with respect to radius squared $r^2$ to optimize the diffraction efficiency. The Fresnel zones are of equal areas. However, within a Fresnel zone, the subzones areas are arbitrarily divided and the subzones are not necessarily of equal areas. This novel type of lens is referred to as a "subzonal multifocal diffractive (SMUD) lens".

As used herein, the term "the same" as in "the division ratios are the same with respect to radius squared $r^2$" may be construed to mean "substantially equal" when small higher order terms are dropped in the mathematical derivation detailed in the following specifications, or "equal within the fabrication tolerances" during manufacturing. Similarly, the term "equal" as in "The Fresnel zones are of equal areas" may be construed to mean "substantially equal" or "approximately the same", when higher order terms are ignored, or "equal within the fabrication tolerances".

The main advantage of a SMUD lens is that it gives lens designers more freedom in phase profile design and thus enables more flexible energy allocation among different diffraction orders, which was not possible before. With careful segmentation of each zone, and proper choice of the diffractive profile of each subzone, multifocal diffractive lenses with desired energy distribution at three or even more foci can be achieved.

A two-subzone SMUD lens with a periodically linear profile in $\rho$ can be expressed as $$\phi(\rho;\lambda) = 2\pi\alpha\beta_s\left(j - \frac{\rho}{2\lambda_0 d'}\right) \quad (20)$$
$$\rho_j \leq \rho < \rho_{j+1}, \rho_j = 2j\lambda_0 d'$$

where $$\beta_s = \begin{cases} \beta_1, & j \leq \frac{\rho}{2\lambda_0 d'} < j+\gamma \\ \beta_2, & j+\gamma \leq \frac{\rho}{2\lambda_0 d'} < j+1 \end{cases} \quad (21)$$

$\gamma$ is a division ratio, and its physical meaning is the ratio of the first type subzone area over a full Fresnel zone area. The phase step factors $\beta_1$ and $\beta_2$ are independent of each other. $\gamma \in [0, 1]$, and when $\gamma=0$ or 1, the two-subzone SMUD lens is reduced to a diffractive lens with a constant phase step factor.

The phase profile of a SMUD lens in Eq.(20), or in more generalized forms described in the following, could be a thickness profile, or a refractive index profile, and the phase profile of each subzone changes with radius r from an inner edge of the subzone to an outer edge of the subzone. The thickness profile could be formed by a lathe by direct machining, or it could be formed by a mold, such as by injection molding. Alternatively, the thickness profile could be formed by optically matching two materials with different refractive indices. The two optical materials could have complementary thickness profiles so that they could be matched with optical adhesives to avoid external sharp edges at the subzone boundaries, including the Fresnel zone boundaries.

The phase profile could also be a refractive index profile, which changes with radius r from an inner edge of the subzone to an outer edge of the subzone. The refractive index profile could be formed by altering the refractive index of a portion of a material of the SMUD lens by laser micromachining. Commonly used lasers in ophthalmology include excimer lasers, femtosecond lasers, etc. The refractive index profile could also be formed by changing the refractive index of a portion of a material of the SMUD lens by doping, or ion exchange, etc.

Because of the periodicity in $\rho$, the transmission function $t(\rho)$ can still be expanded as a Fourier series, and based on Eq.(10), the coefficient $$c_m = \gamma e^{i\pi\gamma(m-\alpha\beta_1)}\text{sinc}[\gamma(m-\alpha\beta_1)]+(1-\gamma)e^{i\pi(1+\gamma)(m-\alpha\beta_2)} \times \text{sinc}[(1-\gamma)(m-\alpha\beta_2)] \quad (22)$$

From Eq.(11), the m-thorder diffraction efficiency $$\eta_m = \gamma^2\text{sinc}^2[\gamma(m-\alpha\beta_1)]+(1-\gamma)^2\text{sinc}^2[(1-\gamma)(m-\alpha\beta_2)]+2\gamma(1-\gamma)\text{sinc}[\gamma(m-\alpha\beta_1)]\text{sinc}[(1-\gamma)(m-\alpha\beta_2)]\cos\{\pi[\gamma(m-\alpha\beta_1)-(1+\gamma)(m-\alpha\beta_2)]\} \quad (23)$$

It is important to point out that $c_m$ and $n_m$ are independent of the choice of the first order focal length d and d'=|d|/n'. Further, the sinc cross-term of different subzones in Eq.(23) is a significant part of the total diffraction efficiency, which can contribute up to 50% of the total diffraction efficiency, and the sinc cross-term can be negative.

The additional freedoms of a different phase step factor and an arbitrary subzonal division ratio $\gamma$ make a two-subzone SMUD lens especially useful for trifocal diffractive lens designs. The next analysis will be focused to find good designs of a trifocal diffractive lens.

When $\gamma=0.5$, all the subzones in the two-subzone SMUD lens are of equal areas. This special case is equivalent to some multifocal diffractive lenses in the prior art. If the subzone numbers (instead of the entire Fresnel zone numbers) are counted, $\gamma=0.5$ corresponds to a design with alternating odd and even numbered zones of equal areas, where all the odd numbered zones share one phase profile in $\rho$ and all the even numbered zones share a different phase profile in $\rho$.

The diffraction efficiency of the two-subzone SMUD lens with $\gamma=0.5$ is $$\eta_m = \tfrac{1}{4}\text{sinc}^2[\tfrac{1}{2}(m-\alpha\beta_1)]+\text{sinc}^2[\tfrac{1}{2}(m-\alpha\beta_2)]+\tfrac{1}{2}\text{sinc}[\tfrac{1}{2}(m-\alpha\beta_1)]\text{sinc}[\tfrac{1}{2}(m-\alpha\beta_2)]\cos\{\pi[\tfrac{1}{2}(m-\alpha\beta_1)-\tfrac{3}{2}(m-\alpha\beta_2)]\} \quad (24)$$

Further, when $\beta_1=\beta_2=\beta$, simple mathematical calculation demonstrates that Eq.(24) is reduced to Eq.(19).

Figure 4:
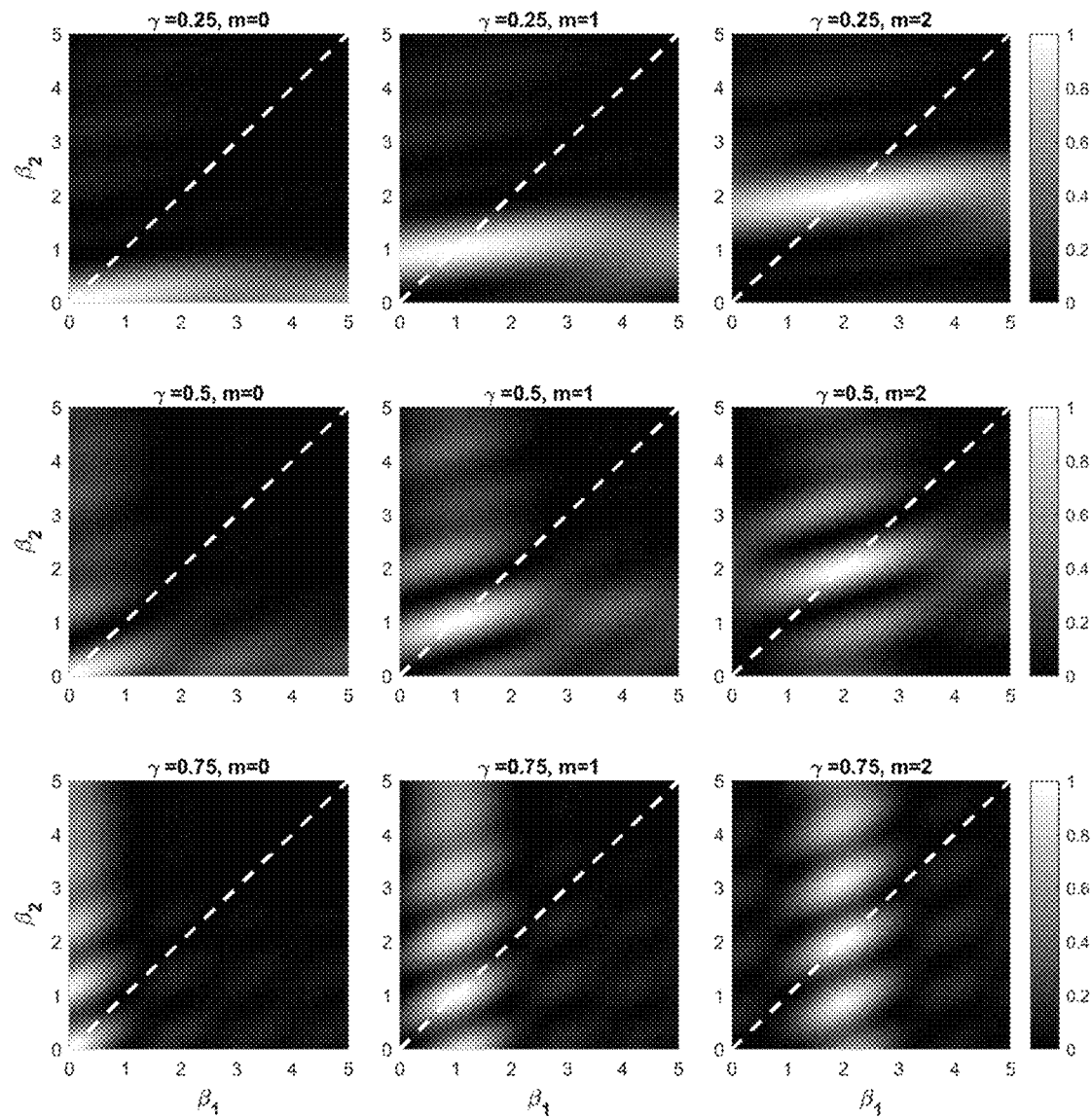
FIG. 4 presents the diffraction efficiency variation with the phase step factors $\beta_1$ and $\beta_2$, both in the range of 0~5, for a two-subzone SMUD lens at the design wavelength $\lambda_0$ ($\alpha=1$) with three representative division ratio values of $\gamma=0.25, 0.5, 0.75$. m is the diffraction order. The grayscale color bar is in linear scale.

FIG. 4 is created with Eq.(23). It presents the diffraction efficiency dependence on different $\beta_1$ and $\beta_2$ pairs of the first three diffraction orders of three two-subzone SMUD lenses with three representative $\gamma=0.25$ (top row), 0.5 (middle row), 0.75 (bottom row) at the design wavelength $\lambda_0$.

Figure 3:
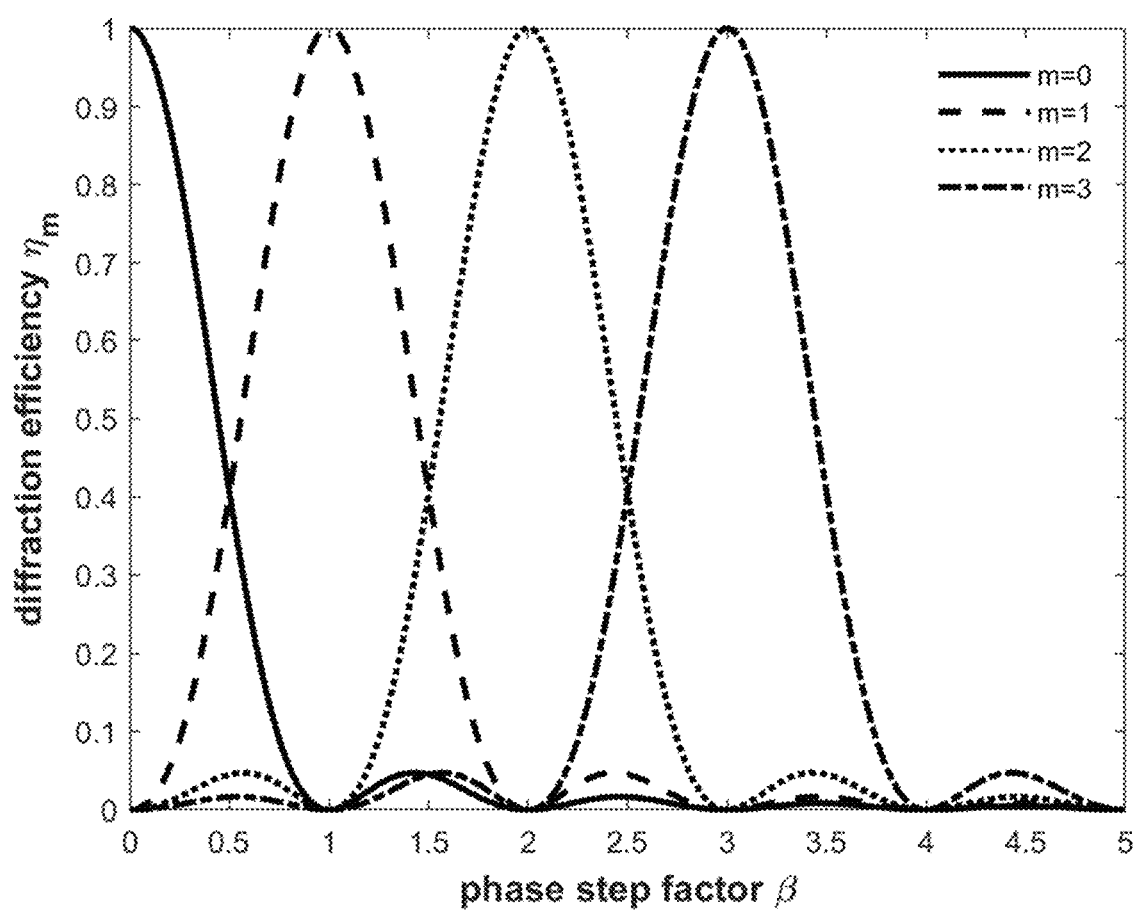
FIG. 3 presents the diffraction efficiency variation of different orders with the phase step factor $\beta$ at the design wavelength $\lambda_0$ ($\alpha=1$).

The dashed diagonal line of $\beta_1=\beta_2$ in each subplot of FIG. 4 presents a lens with a constant phase step factor, which has already been analyzed in FIG. 3. Similar to FIG. 3, the diffraction efficiency pattern in each subplot in FIG. 4 jumps at integer $\beta=m$ along the diagonal line while maintaining exactly the same form.

Figure 5:
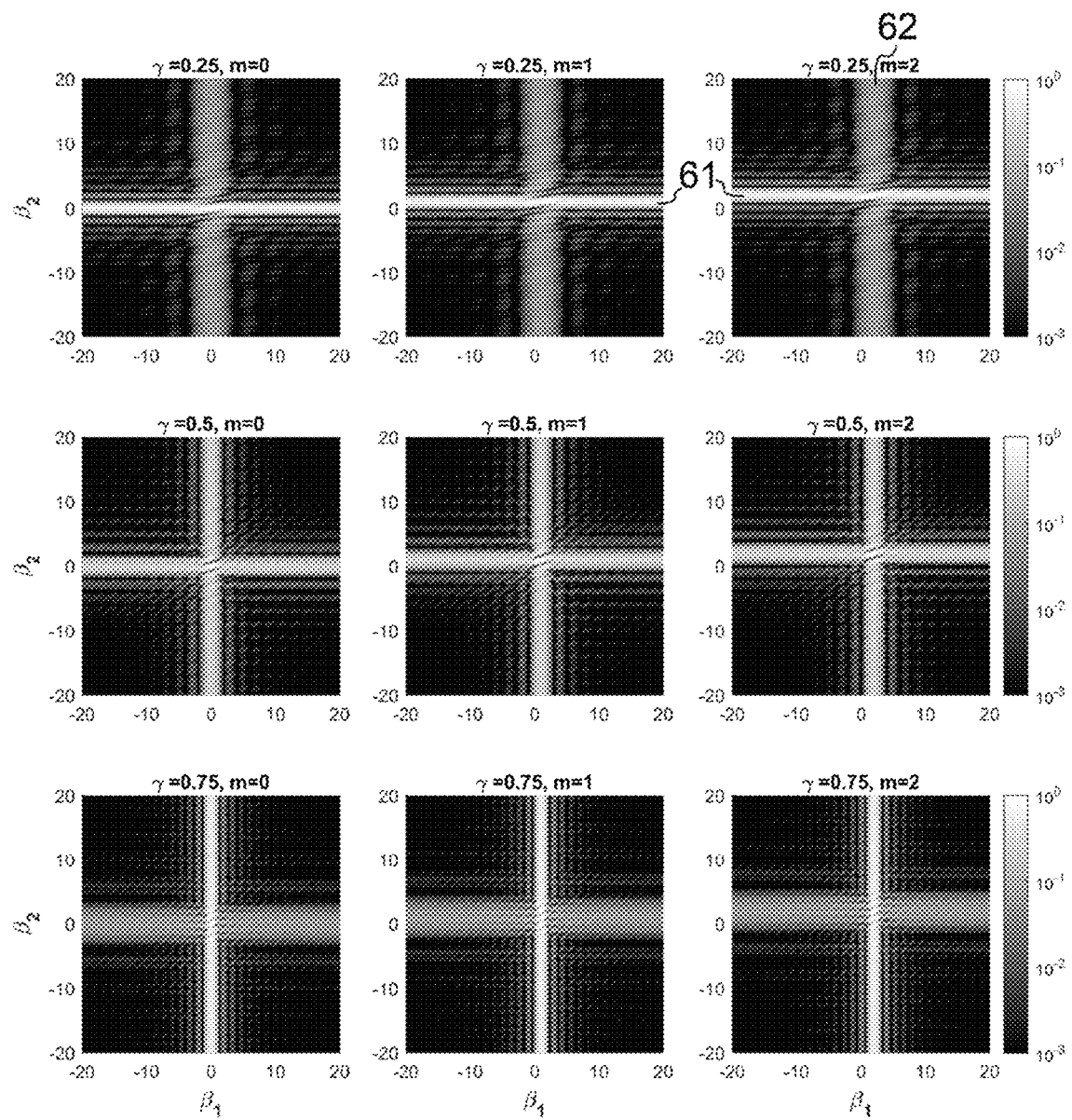
FIG. 5 presents the diffraction efficiency variation with the phase step factors $\beta_1$ and $\beta_2$, both in a larger range of −20~20, at the design wavelength $\lambda_0$ ($\alpha=1$) with three representative division ratio values of $\gamma=0.25, 0.5, 0.75$. The grayscale color bar is in logarithmic scale.

FIG. 5 presents a "zoomed-out" diffraction efficiency plot of the same three two-subzone SMUD lenses as in FIG. 4, but both $\beta_1$ and $\beta_2$ are in a larger range of −20~20. In order to present dim features more clearly, a logarithmic scale color bar is used in FIG. 5, unlike the linear scale color bar used in FIG. 4. A cross pattern is consistent throughout all the subplots in FIG. 5. The cross center is located at $\beta_1=\beta_2=m$, and the two orthogonal lines that form the cross are regions close to the two lines of $\beta_1=m$ and $\beta_2=m$, respectively. At these two lines, at least one subzone is "blazed", i.e. of the optimal shape for maximum diffraction efficiency at the m-th order.

Figure 6:
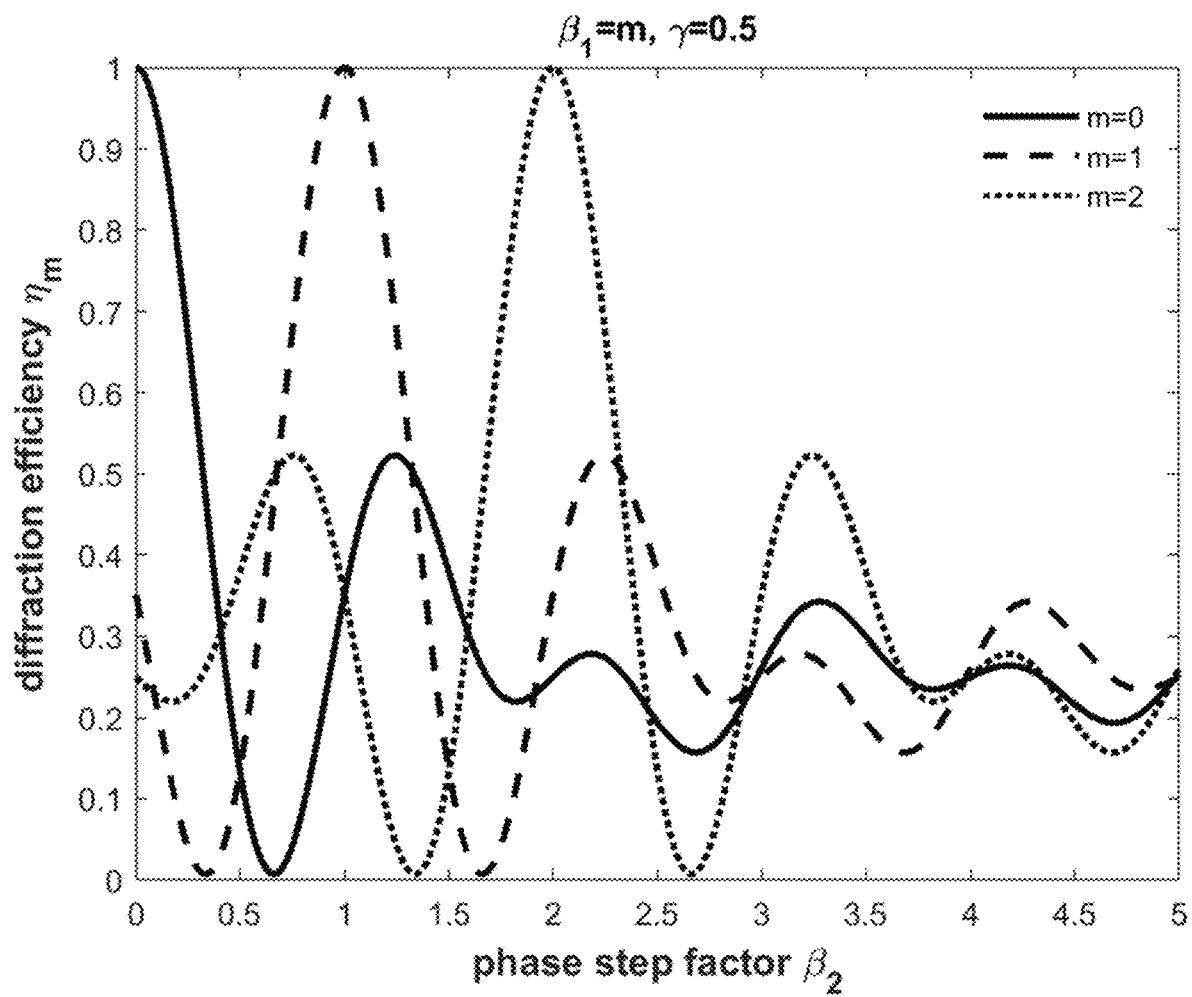
FIG. 6 presents the diffraction efficiency variation with the phase step factors $\beta_2$ for the special case of $\beta_1$=m, $\gamma=0.5$ at the design wavelength $\lambda_0$ ($\alpha=1$).

When $\beta_1=m$, and $\alpha=1$, the diffraction efficiency is $$\eta_m=\gamma^2+(1-\gamma)^2\text{sinc}^2[(1-\gamma)(m-\beta_2)]+2\gamma(1-\gamma)\text{sinc}[(1-\gamma)(m-\beta_2)]\cos[-\pi(1+\gamma)(m-\beta_2)] \quad (25)$$

when $\beta_2\to\infty$, all sinc terms→0, hence, $\eta_m\to\gamma^2$. The specific case of $\gamma=0.5$ is plotted in FIG. 6. It's noticeable that the diffraction efficiencies at different orders sum up to larger than 1 for some $\beta_2$ in FIG. 6. The reason is because FIG. 6 is not the diffraction efficiencies for multiple diffraction orders of the same structure. In a SMUD lens, the subzone profile is completely independent with each other within the same Fresnel zone. Hence, $\beta_1$ and $\beta_2$ are not related. $\beta_1=m$ is assumed in FIG. 6, so the SMUD lens profile changes with the diffraction order m, and the sum of $\eta_m$ of multiple diffraction orders of different lenses can be larger than 1.

When $\beta_2=m$, and $\alpha=1$, the diffraction efficiency is $$\eta_m=(1-\gamma)^2+\gamma^2\text{sinc}^2[\gamma(m-\beta_1)]+2\gamma(1-\gamma)\text{sinc}[\gamma(m-\beta_1)]\cos[\pi\gamma(m-\beta_1)] \quad (26).$$

Figure 7:
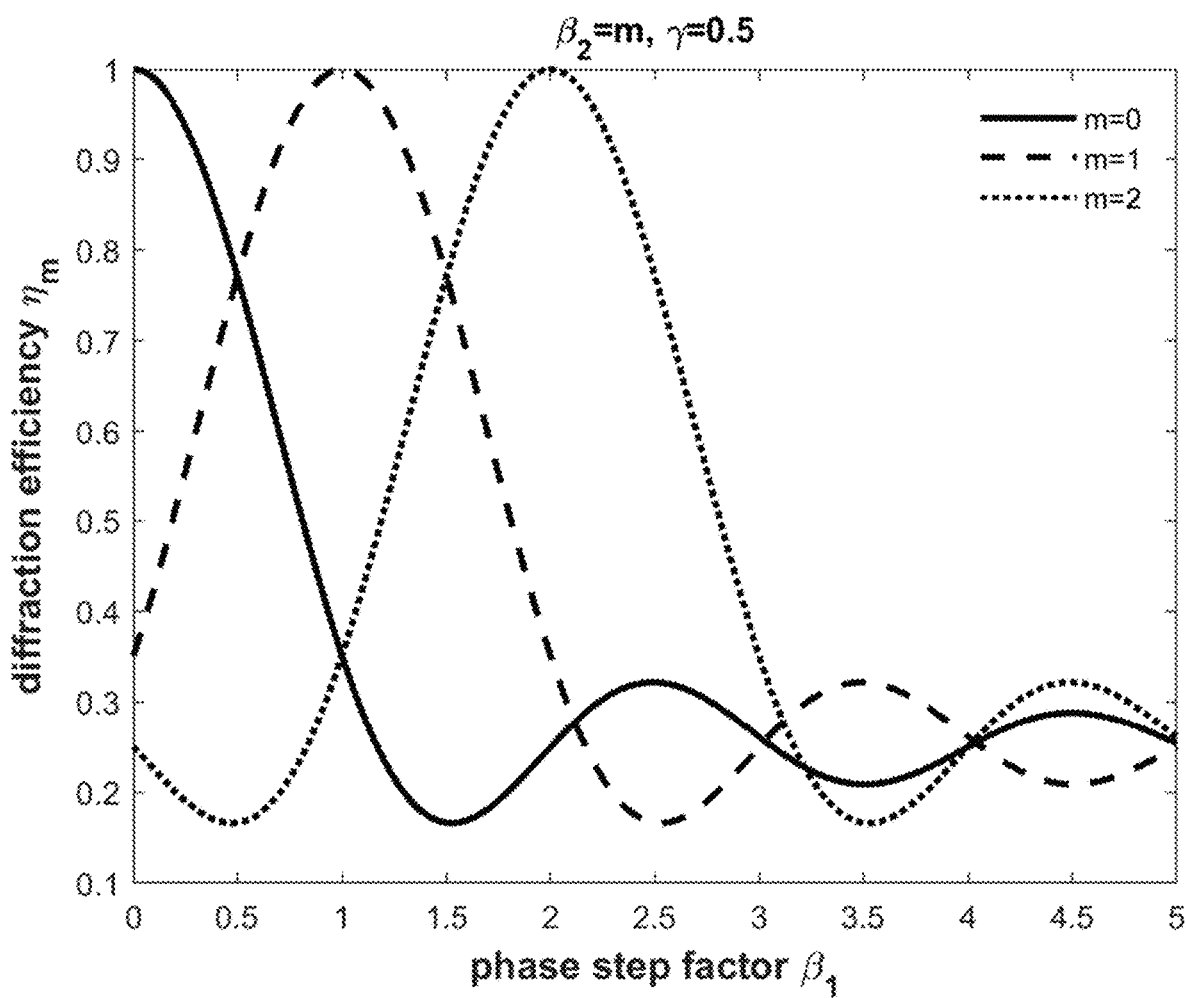
FIG. 7 presents the diffraction efficiency variation with the phase step factors $\beta_1$ for the special case of $\beta_2$=m, $\gamma=0.5$ at the design wavelength $\lambda_0$ ($\alpha=1$).

Similarly, when $\beta_1\to\infty$, all sinc terms→0, hence, $\eta_m\to(1-\gamma)^2$. The specific case of $\gamma=0.5$ is plotted in FIG. 7.

The above analysis can be used to explain the cross feature in FIG. 5. For example, at $\gamma=0.25$, the bright horizontal line 61 of the cross at large $\beta_1$ corresponds to $\eta_m\to(1-0.25)^2=0.5625$, while the relatively dimmer vertical line 62 of the cross at large $\beta_2$ corresponds to $\eta_m\to0.25^2=0.0625$. At $\gamma=0.75$, the diffraction efficiency of these two lines of the cross are of the opposite values. At $\gamma=0.5$, both lines of the cross correspond to $\eta_m\to0.5^2=0.25$.

For a trifocal design of a two-subzone SMUD lens, the zeroth, first and second diffraction orders will be analyzed for the phase step in the range of $\beta_1, \beta_2 \in [0, 2]$. This relatively small range of $\beta$ is chosen in order to have good diffraction efficiencies in the entire visible spectrum.

Depending on the desired diffraction efficiency allocation among different orders, different merit function can be used to find a good trifocal design solution space. For example, if equal energy splitting is desired for the three foci in the trifocal design, a parameter of the sum of squares (SS) can be used:

$$SS=(\eta_0-\eta_1)^2+(\eta_0-\eta_2)^2+(\eta_1-\eta_2)^2 \quad (27)$$

By minimizing SS, designs of $\beta_1, \beta_2$ that correspond to substantially equal diffraction energy output can be obtained.

More generally, the sum of squares can be defined as:

$$SS=\left(\frac{\eta_0}{w_0}-\frac{\eta_1}{w_1}\right)^2+\left(\frac{\eta_0}{w_0}-\frac{\eta_2}{w_2}\right)^2+\left(\frac{\eta_1}{w_1}-\frac{\eta_2}{w_2}\right)^2 \quad (28)$$

where $w_0$, $w_1$, and $w_2$ are the weighting factors, and $w_0:w_1:w_2$ represents the desired diffraction efficiency splitting ratio of the first three orders.

Meanwhile, in a trifocal design using the first three orders, light diffracted into higher orders is not used and serves as a background that will lower the image contrast. The effective diffraction efficiency of the first three orders is $$\eta_{eff}=\eta_0+\eta_1+\eta_2 \quad (29)$$

A good design will have desired diffraction efficiency splitting ratio, i.e. a minimized SS, while maximizing the effective diffraction efficiency $\eta_{eff}$, and there is often a trade-off between these two goals.

As a numerical analysis example, trifocal designs with equal energy splitting, i.e. the weighting factor target of $w_0:w_1:w_2=1:1:1$ are searched. The search is done for the design wavelength $\lambda_0$ ($\alpha=1$), with $\gamma$ in the range of 0~1 with an increment of 0.01, and both $\beta_1$ and $\beta_2$ in the range of 0~2 with an increment of 0.01, for chromatic control. If the conditions of SS<0.001 and $\eta_{eff}$>80% are required, a total of 362 trifocal design solutions can be found with $\gamma$ in the range of [0.42, 0.62], the maximum $\eta_{eff,max}$=84.71%, and the minimum $SS_{min}$=2.3×10$^{-6}$.

Table 1 lists several representative trifocal design solutions that meet the above requirements. Design #1 and #2 are for $\gamma=0.5$, which means the subzones are of equal areas, and they form an antisymmetric pair. Design #3 and #4 generate the largest effective diffraction efficiency gar of about 85%. The profile of Design #3 and #4 are present in FIG. 8 and FIG. 9. Design #5 and #6 give the smallest SS, which means the energy is most evenly distributed in the three orders. Within current design space, effective diffraction efficiency larger than 85% is achievable, however, the energy won't be as evenly distributed, i.e. those designs will have an SS larger than 0.001. With this trade-off, the final choice of a good multifocal design is application-determined.

TABLE 1

| # | $\gamma$ | $\beta_1$ | $\beta_2$ | $\eta_0$ | $\eta_1$ | $\eta_2$ | $\eta_{eff}$ | SS |
|---|---|---|---|---|---|---|---|---|
| 1 | 0.50 | 0.68 | 1.31 | 28.18% | 28.43% | 27.68% | 84.29% | 8.7 × 10$^{-5}$ |
| 2 | 0.50 | 1.32 | 0.69 | 27.68% | 28.43% | 28.18% | 84.29% | 8.7 × 10$^{-5}$ |
| 3 | 0.51 | 0.73 | 1.32 | 27.21% | 29.32% | 28.19% | 84.71% | 6.7 × 10$^{-4}$ |
| 4 | 0.51 | 1.27 | 0.68 | 28.19% | 29.32% | 27.21% | 84.71% | 6.7 × 10$^{-4}$ |
| 5 | 0.44 | 0.47 | 1.28 | 27.10% | 27.09% | 27.20% | 81.39% | 2.3 × 10$^{-6}$ |
| 6 | 0.44 | 1.53 | 0.72 | 27.20% | 27.09% | 27.10% | 81.39% | 2.3 × 10$^{-6}$ |

Figure 8:
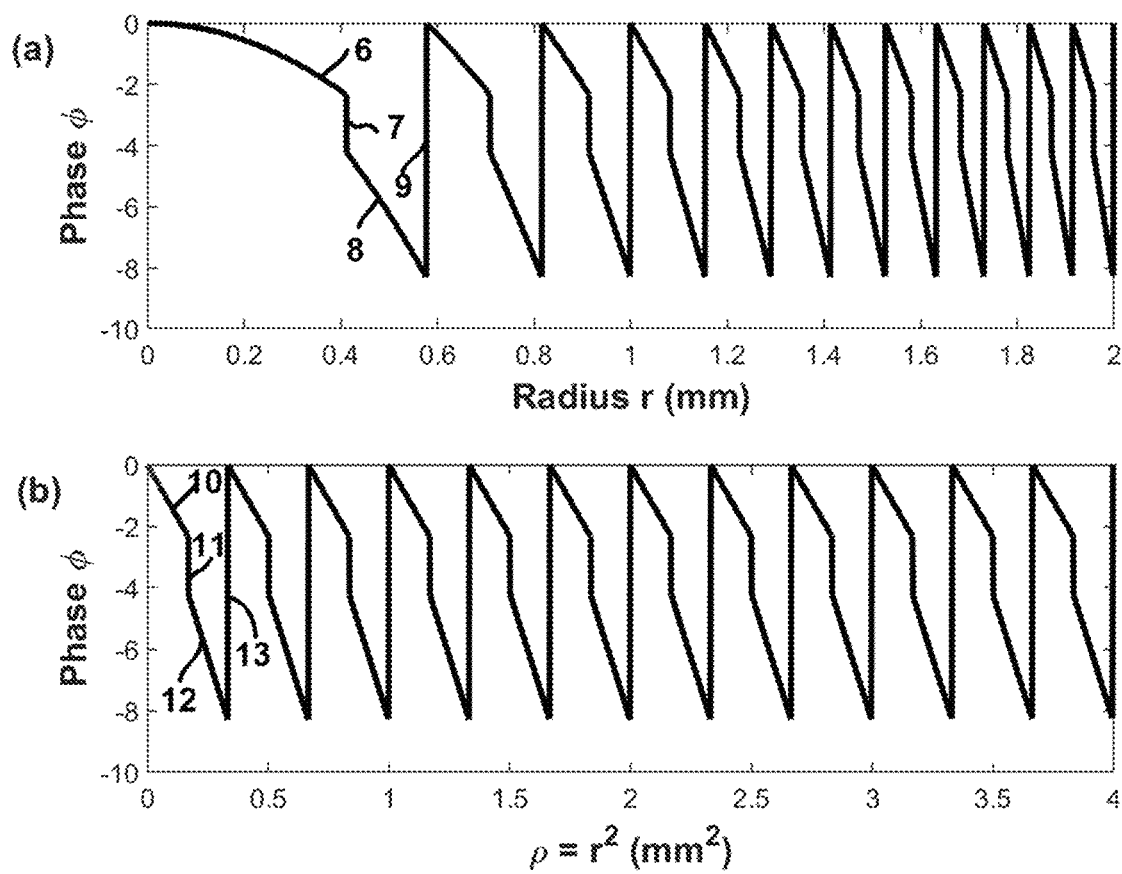
FIGS. 8 and 9 present two phase profiles of trifocal lenses with respect to radius r and $\rho$. The phase profile is periodically linear in $\rho$.

FIGS. 8(*a*) and 8(*b*) present the phase profile of a trifocal lens (Design #3) with respect to radius r and $\rho=r^2$. The phase profile is periodically linear in $\rho$. The specific design parameters of this profile are: $\lambda_0$=555 nm, d'=300 mm, $\alpha$=1, $\beta_1$=0.73, $\beta_2$=1.32, $\gamma$=0.51. FIG. 8(*a*) presents the phase profile 6 of the first type subzone; the phase step 7 between the first type subzone and the second type subzone; the phase profile 8 of the second type subzone; and the phase step 9 between the first Fresnel zone and the second Fresnel zone. In FIG. 8(*b*), 10~13 are the corresponding structures of 6~9 plotted with respect top.

Figure 9:
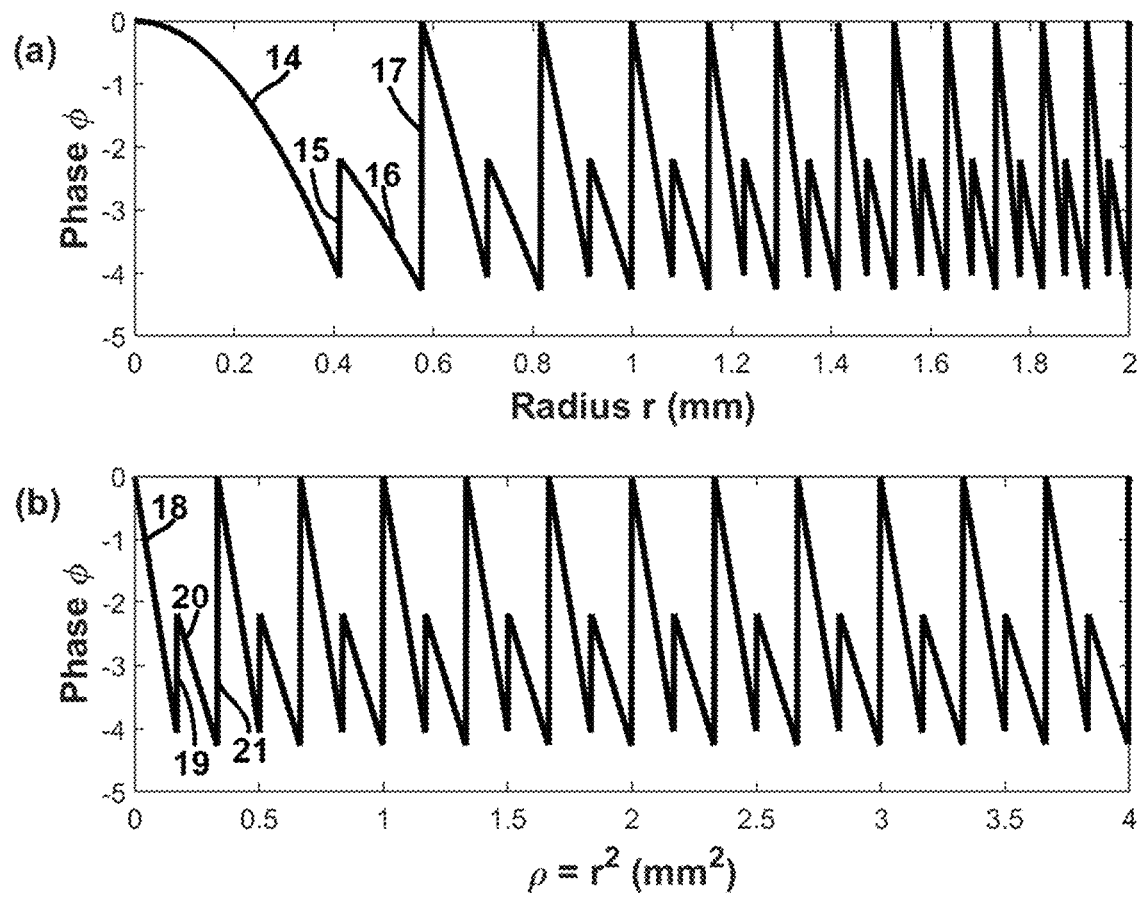

FIGS. 9(*a*) and 9(*b*) present the phase profile of a trifocal lens (Design #4) with respect to radius r and $\rho=r^2$. The phase profile is periodically linear in $\rho$. The specific design parameters of this profile are: $\lambda_0$=555 nm, d'=300 mm, $\alpha$=1, $\beta_1$=1.27, $\beta_2$=0.68, $\gamma$=0.51. FIG. 9(*a*) presents the phase profile 14 of the first type subzone; the phase step 15 between the first type subzone and the second type subzone; the phase profile 16 of the second type subzone; and the phase step 17 between the first Fresnel zone and the second Fresnel zone. In FIG. 9(*b*), 18~21 are the corresponding structures of 14~17 plotted with respect top.

In a preferred embodiment of intraocular lenses, distant vision, which usually corresponds to the zeroth order diffraction, is emphasized. As another numerical analysis example, the same search range and requirements (SS<0.001 and $\eta_{eff}$>80%) as before are used except a different set of weighting factors of $w_0:w_1:w_2$=2:1:1. A total of 474 trifocal design solutions are found with $\gamma$ in the range of [0.40, 0.61], the maximum $\eta_{eff,max}$=84.30%, and the minimum $SS_{min}$=1.9×10$^{-6}$.

Table 2 lists several representative trifocal design solutions to emphasize the zeroth order diffraction. Design #7 and #8 are for $\gamma$=0.5 of equal-area subzones. Design #8 and #9 generate two largest effective diffraction efficiency $\eta_{eff}$>84%. Design #10 and #11 give two smallest SS, which means the zeroth order energy is almost twice that of the other two orders.

TABLE 2

| # | $\gamma$ | $\beta_1$ | $\beta_2$ | $\eta_0$ | $\eta_1$ | $\eta_2$ | $\eta_{eff}$ | SS |
|---|---|---|---|---|---|---|---|---|
| 7 | 0.50 | 1.08 | 0.57 | 41.54% | 20.95% | 21.35% | 83.83% | 5.3 × 10$^{-5}$ |
| 8 | 0.50 | 1.04 | 0.56 | 42.85% | 21.54% | 19.89% | 84.28% | 5.1 × 10$^{-4}$ |
| 9 | 0.49 | 1.05 | 0.56 | 43.33% | 21.33% | 19.63% | 84.30% | 7.2 × 10$^{-4}$ |
| 10 | 0.43 | 1.27 | 0.60 | 40.80% | 20.50% | 20.50% | 81.81% | 1.9 × 10$^{-6}$ |
| 11 | 0.56 | 0.56 | 1.28 | 40.95% | 20.37% | 20.45% | 81.77% | 2.0 × 10$^{-6}$ |

The SMUD lenses that have been analyzed so far are of two-subzones. SMUD lenses with more subzones can be mathematically described by Eq.(20) and a generalized $\beta_s$ of G subzones:

$$\beta_s = \begin{cases} \beta_1, & j \leq \frac{\rho}{2\lambda_0 d'} < j+\gamma_1 \\ \beta_2, & j+\gamma_1 \leq \frac{\rho}{2\lambda_0 d'} < j+\gamma_2 \\ \cdots \\ \beta_g, & j+\gamma_{g-1} \leq \frac{\rho}{2\lambda_0 d'} < j+\gamma_g \\ \cdots \\ \beta_G, & i+\gamma_{G-1} \leq \frac{\rho}{2\lambda_0 d'} < j+\gamma_G = j+1 \end{cases} \quad (30)$$

where the division ratios $\gamma_1 < \gamma_2 < \gamma_g < \gamma_G = 1$.

From Eq.(10), (20) and (30), it can be calculated that the generalized Fourier coefficient is $$c_m = \gamma_1 e^{i\pi\gamma_1(m-\alpha\beta_1)}\text{sinc}[\gamma_1(m-\alpha\beta_1)] + (\gamma_2-\gamma_1) e^{i\pi(\gamma_2+\gamma_1)(m-\alpha\beta_2)}\text{sinc}[(\gamma_2-\gamma_1)(m-\alpha\beta_2)] + \cdots + (\gamma_g-\gamma_{g-1}) e^{i\pi(\gamma_g+\gamma_{g-1})(m-\alpha\beta_g)}\text{sinc}[(\gamma_g-\gamma_{g-1})(m-\alpha\beta_g)] + \cdots + (1-\gamma_{G-1}) e^{i\pi(1+\gamma_{G-1})(m-\alpha\beta_G)}\text{sinc}[(1-\gamma_{G-1})(m-\alpha\beta_G)] \quad (31)$$

Based on Eq.(11) and Eq.(31), diffraction efficiencies $\eta_m$ and other related key design parameters can be designed and evaluated for these generalized SMUD lenses with more foci.

When G=2, the general design is reduced to a two-subzone SMUD lens, and Eq.(31) reduces to Eq.(22).

When G=3, the general design is reduced to a three-subzone SMUD lens, which is suitable to be used as a quadrifocal lens, and Eq.(31) reduces to $$c_m = \gamma_1 e^{i\pi\gamma_1(m-\alpha\beta_1)}\text{sinc}[\gamma_1(m-\alpha\beta_1)] + (\gamma_2-\gamma_1) e^{i\pi(\gamma_2+\gamma_1)(m-\alpha\beta_2)}\text{sinc}[(\gamma_2-\gamma_1)(m-\alpha\beta_2)] + (1-\gamma_2) e^{i\pi(1+\gamma_2)(m-\alpha\beta_3)}\text{sinc}[(1-\gamma_2)(m-\alpha\beta_3)] \quad (32)$$

Based on Eq.(11) and Eq.(32), the m-th order diffraction efficiency of a three-subzone SMUD lens is $$\eta_m = \gamma_1^2\text{sinc}^2[\gamma_1(m-\alpha\beta_1)] + (\gamma_2-\gamma_1)^2\text{sinc}^2[(\gamma_2-\gamma_1)(m-\alpha\beta_2)] + (1-\gamma_2)^2\text{sinc}^2[(1-\gamma_2)(m-\alpha\beta_3)] + 2\gamma_1(\gamma_2-\gamma_1)\text{sinc}[\gamma_1(m-\alpha\beta_1)]\text{sinc}[(\gamma_2-\gamma_1)(m-\alpha\beta_2)]\cos\{\pi[\gamma_1(m-\alpha\beta_1)-(\gamma_2+\gamma_1)(m-\alpha\beta_2)]\} + 2\gamma_1(1-\gamma_2)\text{sinc}[\gamma_1(m-\alpha\beta_1)]\text{sinc}[(1-\gamma_2)(m-\alpha\beta_3)]\cos\{\pi[\gamma_1(m-\alpha\beta_1)-(1+\gamma_2)(m-\alpha\beta_3)]\} + 2(\gamma_2-\gamma_1)(1-\gamma_2)\text{sinc}[(\gamma_2-\gamma_1)(m-\alpha\beta_2)]\text{sinc}[(1-\gamma_2)(m-\alpha\beta_3)]\cos\{\pi[(\gamma_2+\gamma_1)(m-\alpha\beta_2)-(1+\gamma_2)(m-\alpha\beta_3)]\} \quad (33)$$

Based on Eq.(33), the three-subzone SMUD lens design solutions for quadrifocal diffractive lenses can be analyzed. For a quadrifocal lens, the sum of squares can be defined as:

$$SS = \left(\frac{\eta_0}{w_0} - \frac{\eta_1}{w_1}\right)^2 + \left(\frac{\eta_0}{w_0} - \frac{\eta_2}{w_2}\right)^2 + \left(\frac{\eta_0}{w_0} - \frac{\eta_3}{w_3}\right)^2 + \left(\frac{\eta_1}{w_1} - \frac{\eta_2}{w_2}\right)^2 + \left(\frac{\eta_1}{w_1} - \frac{\eta_3}{w_3}\right)^2 + \left(\frac{\eta_2}{w_2} - \frac{\eta_3}{w_3}\right)^2, \quad (34)$$

where $w_0$, $w_1$, $w_2$ and $w_3$ are the weighting factors of the first four orders.

The effective diffraction efficiency of the first four orders is $$\eta_{eff} = \eta_0 + \eta_1 + \eta_2 + \eta_3 \quad (35)$$

As another numerical analysis example, quadrifocal designs with equal energy splitting, i.e. the weighting factor target of $w_0:w_1:w_2:w_3$=1:1:1:1 are analyzed. The analysis is done for the design wavelength $\lambda_0$ ($\alpha$=1), with $\gamma_1$ and $\gamma_2$ in the range of 0~1 with an increment of 0.1, and $\gamma_1 < \gamma_2$. $\beta_1$, $\beta_2$ and $\beta_3$ are all in the range of 0~3 with an increment of 0.1. If the conditions of SS<0.01 and $\eta_{eff}$>80% are required, the maximum $\eta_{eff,max}$=88.5%, and the minimum $SS_{min}$=4.0×10$^{-4}$ are found.

Table 3 lists several representative quadrifocal design solutions that meet the above requirements. Design #12~#15 all have $\gamma_1$=0, which means the three-subzone SMUD lens design is reduced to a two-subzone SMUD lens design, which has already been described. When $\gamma_1$=0, $\beta_1$ doesn't correspond to any structural parameter, so $\beta_1$ can be any number and won't affect the physical lens shape. Design #16 and #17 have the largest $\eta_{eff,max}$=88.5%, while design #18 and #19 have the smallest $SS_{min}$=4.0×10$^{-4}$ within the search range.

TABLE 3

| # | $\gamma_1$ | $\gamma_2$ | $\beta_1$ | $\beta_2$ | $\beta_3$ |
|---|---|---|---|---|---|
| 12 | 0 | 0.5 | — | 0.5 | 2.5 |
| 13 | 0 | 0.5 | — | 2.5 | 0.5 |
| 14 | 0 | 0.6 | — | 2.3 | 0.4 |
| 15 | 0 | 0.6 | — | 0.7 | 2.6 |
| 16 | 0.4 | 0.7 | 2.1 | 0.9 | 0.8 |
| 17 | 0.4 | 0.7 | 0.9 | 2.1 | 2.2 |
| 18 | 0.4 | 0.8 | 2.2 | 0.9 | 0.8 |
| 19 | 0.4 | 0.8 | 0.8 | 2.1 | 2.2 |

| # | $\eta_0$ | $\eta_1$ | $\eta_2$ | $\eta_3$ | $\eta_{eff}$ | SS |
|---|---|---|---|---|---|---|
| 12 | 21.1% | 22.5% | 22.5% | 21.1% | 87.2% | 8.3 × 10$^{-4}$ |
| 13 | 21.1% | 22.5% | 22.5% | 21.1% | 87.2% | 8.3 × 10$^{-4}$ |
| 14 | 23.1% | 23.4% | 21.6% | 18.5% | 86.5% | 6.0 × 10$^{-3}$ |
| 15 | 18.5% | 21.6% | 23.4% | 23.1% | 86.5% | 6.0 × 10$^{-3}$ |
| 16 | 23.9% | 23.6% | 22.1% | 18.8% | 88.5% | 6.6 × 10$^{-3}$ |
| 17 | 18.8% | 22.1% | 23.6% | 23.9% | 88.5% | 6.6 × 10$^{-3}$ |
| 18 | 21.8% | 22.7% | 21.5% | 21.5% | 87.5% | 4.0 × 10$^{-4}$ |
| 19 | 21.5% | 21.5% | 22.7% | 21.8% | 87.5% | 4.0 × 10$^{-4}$ |

Figure 10:
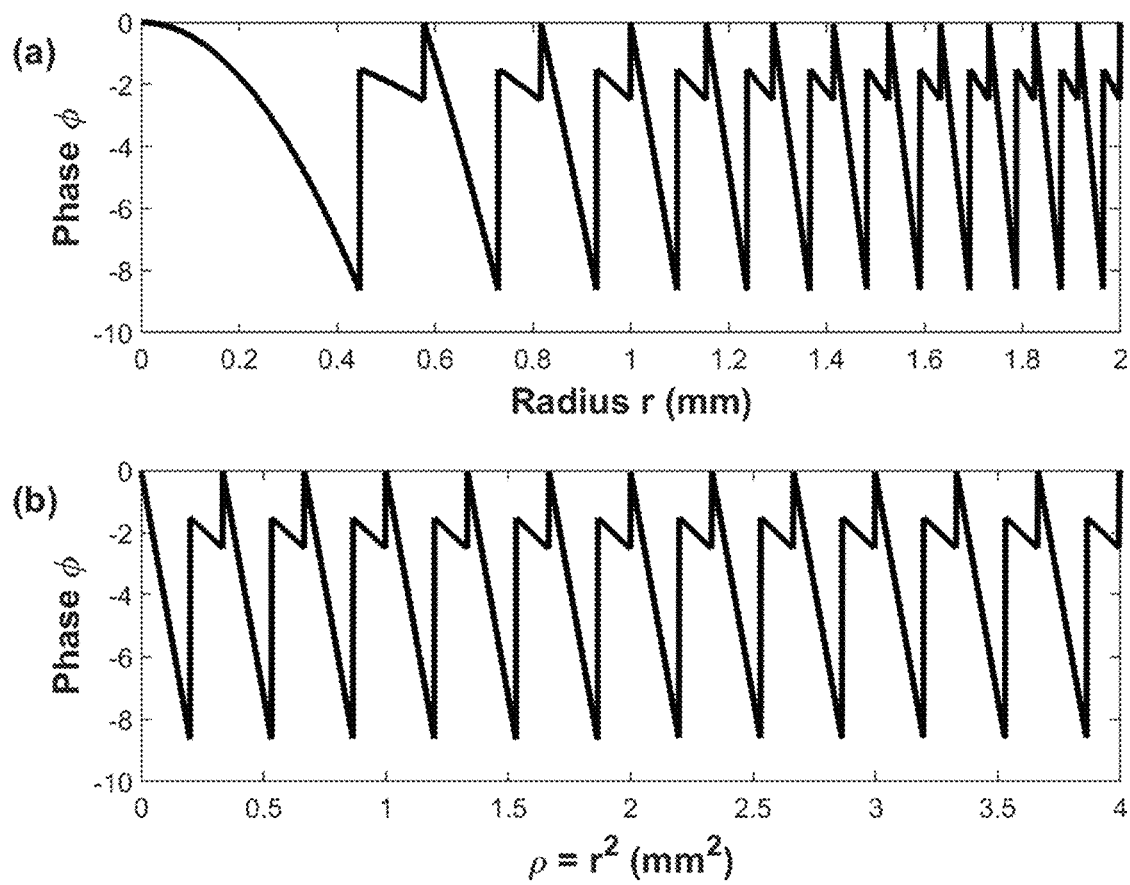
FIGS. 10 to 13 present four representative phase profiles of quadrifocal lenses with respect to radius r and $\rho$. The phase profile is periodically linear in $\rho$.

FIG. 10 presents the phase profile of a two-subzone quadrifocal lens (Design #14) with respect to radius r in 10(*a*) and ρ in 10(*b*). The phase profile is periodically linear in ρ. The specific design parameters of this profile are: $\lambda_0$=555 nm, d'=300 mm, α=1, $\gamma_1$=0, $\gamma_2$=0.6, $\beta_1$=any number, $\beta_2$=2.3, $\beta_3$=0.4.

Figure 11:
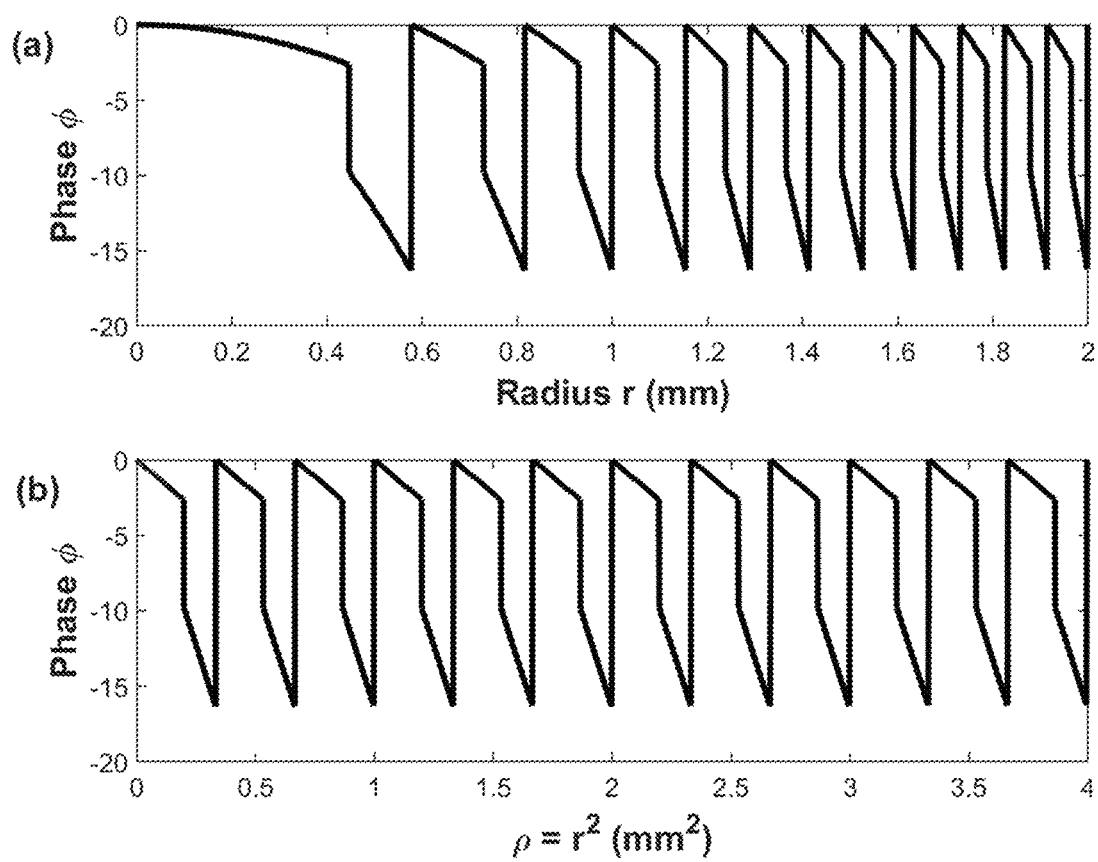

FIG. 11 presents the phase profile of a two-subzone quadrifocal lens (Design #15) with respect to radius r in 11(*a*) and ρ in 11(*b*). The phase profile is periodically linear in ρ. The specific design parameters of this profile are: $\lambda_0$=555 nm, d'=300 mm, α=1, $\gamma_1$=0, $\gamma_2$=0.6, $\beta_1$=any number, $\beta_2$=0.7, $\beta_3$=2.6.

Figure 12:
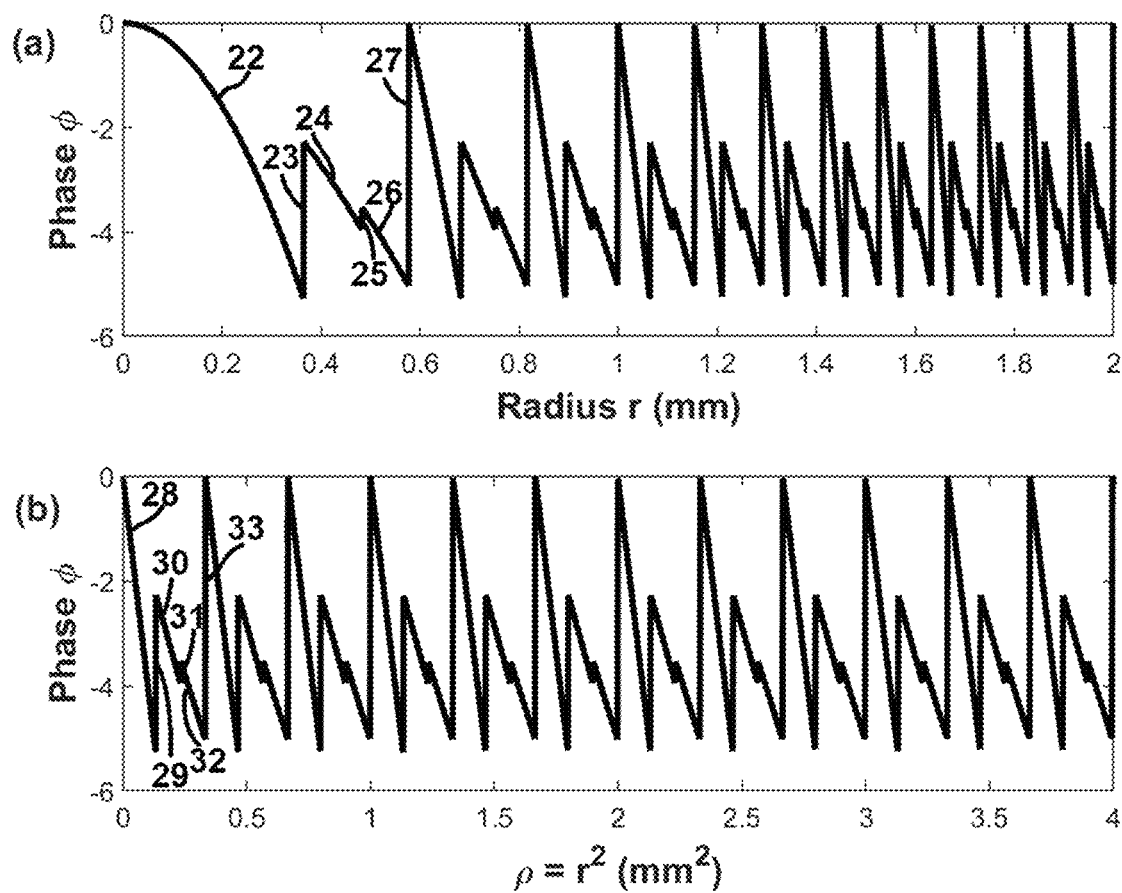

FIG. 12 presents the phase profile of a three-subzone quadrifocal lens (Design #16) with respect to radius r in 12(*a*) and ρ in 12(*b*). The phase profile is periodically linear in ρ. The specific design parameters of this profile are: $\lambda_0$=555 nm, d'=300 mm, α=1 $\gamma_1$=0.4, $\gamma_2$=0.7, $\beta_1$=2.1, $\beta_2$=0.9, $\beta_3$=0.8. FIG. 12(*a*) presents the phase profile 22 of the first type subzone; the phase step 23 between the first type subzone and the second type subzone; the phase profile 24 of the second type subzone; the phase step 25 between the second type subzone and the third type subzone; the phase profile 26 of the third type subzone; and the phase step 27 between first Fresnel zone and the second Fresnel zone. In FIG. 12(*b*), 28~33 are the corresponding structures of 22~27 plotted with respect to ρ=r².

Figure 13:
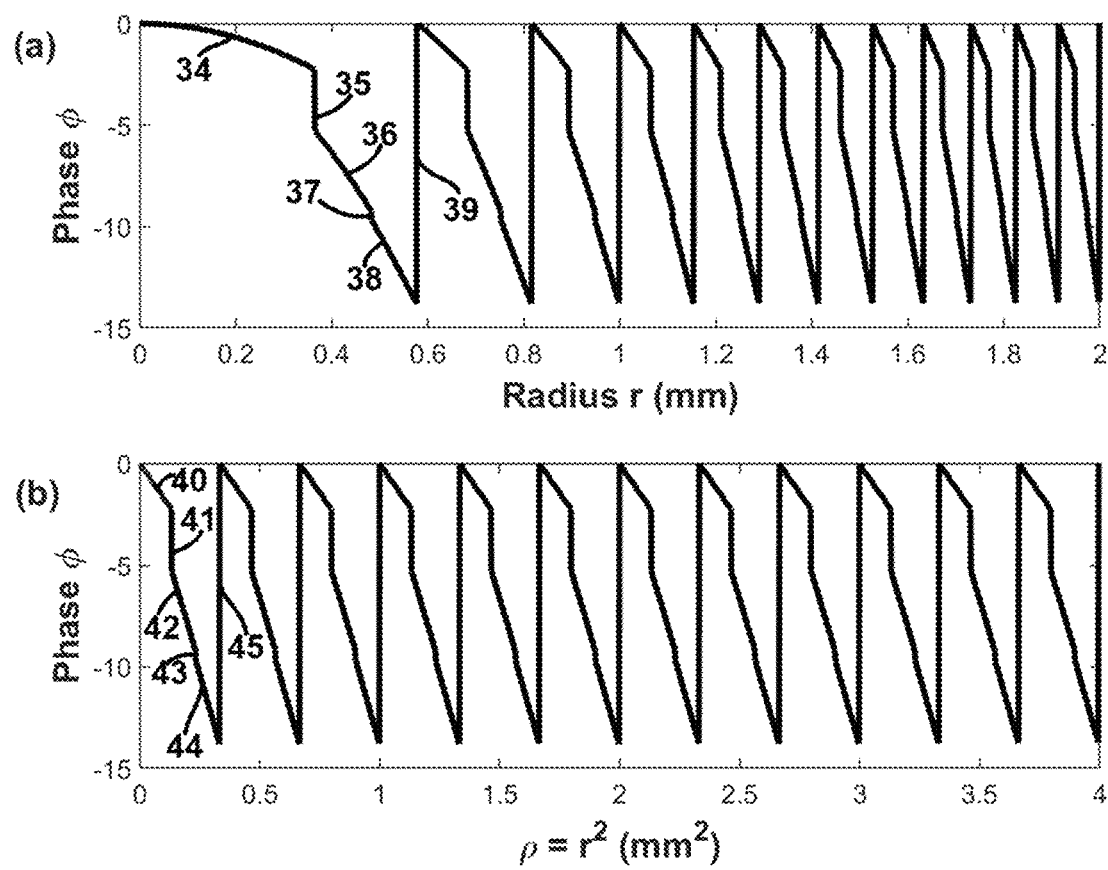

FIG. 13 presents the phase profile of a three-subzone quadrifocal lens (Design #17) with respect to radius r in 13(*a*) and ρ in 13(*b*). The phase profile is periodically linear in ρ. The specific design parameters of this profile are: $\lambda_0$=555 nm, d'=300 mm, α=1, $\gamma_1$=0.4, $\gamma_2$=0.7, $\beta_1$=0.9, $\beta_2$=2.1, $\beta_3$=2.2. FIG. 13(*a*) presents the phase profile 34 of the first type subzone; the phase step 35 between the first type subzone and the second type subzone; the phase profile 36 of the second type subzone; the phase step 37 between the second type subzone and the third type subzone; the phase profile 38 of the third type subzone; and the phase step 39 between the first Fresnel zone and the second Fresnel zone.

In FIG. 13(*b*), 40~45 are the corresponding structures of 34~39 plotted with respect to ρ=r².

One surprising result is that some of the best performing quadrifocal lenses are two-subzone SMUD lenses, instead of three-subzone SMUD lenses. Two-subzone SMUD lenses are potentially easier to manufacture for some fabrication methods. Furthermore, quadrifocal lenses with other weighting factor targets can be analyzed following a similar procedure.

SMUD lenses with five or more orders can be analyzed in a similar fashion. However, there is a trade-off between the number of foci of a diffractive lens in use, i.e. the number of object planes in focus and the image contrast. Generally speaking, the more orders and foci a diffractive lens has, the less light is concentrated into any single order and the light of all other orders serves as background noise that will reduce the image contrast. Further, chromatic aberrations tend to be larger at higher diffraction orders, which will limit the operational spectral range. The fine balance is application-dependent.

The diffractive lenses analyzed so far have been chosen to have a diffractive surface profile periodically linear in ρ, due to simplicity. However, a more generalized diffractive lens profile can be expressed as $$\phi(\rho;\lambda) = -2\pi\alpha\beta_s\left(\frac{\rho}{2\lambda_0 d'} - j\right)^{\epsilon_s} \quad (36)$$

where $\epsilon_s$ is an exponent for the corresponding subzone. For example, $\epsilon_s$=1 corresponds to a profile that is linear in ρ and quadratic in r. $\epsilon_s$=1.5 corresponds to a profile that is cubic in r. $\epsilon_s$=2 corresponds to a profile that is quadratic in ρ and quartic in r. The negative sign in Eq.(36) ensures that a positive β corresponds to a positive power.

An even more generalized form of a subzonal multifocal diffractive surface profile could be expressed as $$\phi(\rho;\lambda) = -2\pi\alpha\beta_s\sum_{k=0}^{\infty} a_{sk}\left(\frac{\rho}{2\lambda_0 d'} - j\right)^k \quad (37)$$

where $a_{sk}$ is the coefficient of the k-th exponent of the s-th subzone. The phase profile of each subzone is expressed as a power series of (ρ/2$\lambda_0$d'−j).

Figure 14:
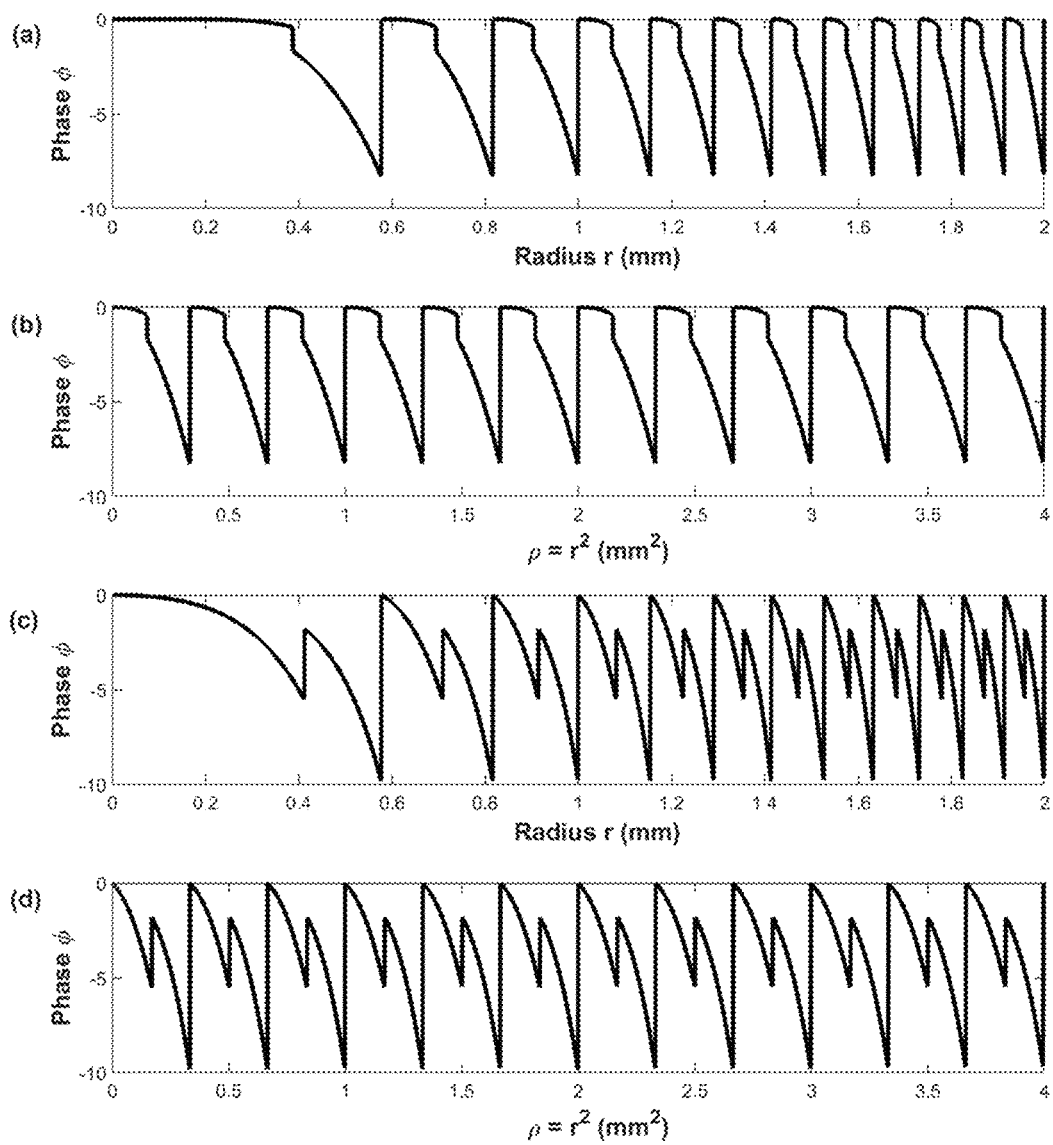
FIG. 14 presents two representative designs where the phase profiles are nonlinear in $\rho$.

FIG. 14 presents two exemplary lenses with nonlinear profiles in ρ. These two profiles are not optimized for diffraction efficiencies, instead they are intended to present possible profiles of generalized SMUD lenses. FIG. 14 (*a*) and (*b*) are of a two-subzone SMUD lens that can be described by Eq.(36), with γ=0.45, $\epsilon_1$=3, i.e. a profile cubic in ρ and hexic in r for the first type subzone; and $\epsilon_2$=2, i.e. a profile quadratic in ρ and quartic in r for the second type subzone.

FIG. 14 (*c*) and (*d*) are of a representative two-subzone SMUD lens that can be described by Eq.(37), and γ=0.51. The first type subzone has the form of $$\phi(\rho) = -2.54\pi\left[0.5\left(\frac{\rho}{2\lambda_0 d'} - j\right) + 1.5\left(\frac{\rho}{2\lambda_0 d'} - j\right)^2 + 0.35\left(\frac{\rho}{2\lambda_0 d'} - j\right)^3\right] \quad (38)$$

and the second type subzone has the form of $$\phi(\rho) = -1.36\pi\left[0.2\left(\frac{\rho}{2\lambda_0 d'} - j\right) + 0.5\left(\frac{\rho}{2\lambda_0 d'} - j\right)^2 + 1.2\left(\frac{\rho}{2\lambda_0 d'} - j\right)^3 + 0.4\left(\frac{\rho}{2\lambda_0 d'} - j\right)^4\right] \quad (39)$$

The diffraction efficiencies of these lenses with nonlinear profiles in ρ can be analyzed to select high diffraction efficiency designs in a similar procedure as in the previous analysis. Further optimization of a SMUD lens profile can be done with the aid of an optical design software to minimize optical aberration while maximizing diffraction efficiencies.

The above analysis are for plane wave incidence with the diffractive surface on a flat substrate. However, sometimes, the diffractive surfaces should be optimized for converging or diverging beam incidence. For example, in the case of an intraocular lens, because the cornea has a positive power of about 43 diopters, the incident light on the intraocular lens is already a converging beam.

Figure 15:
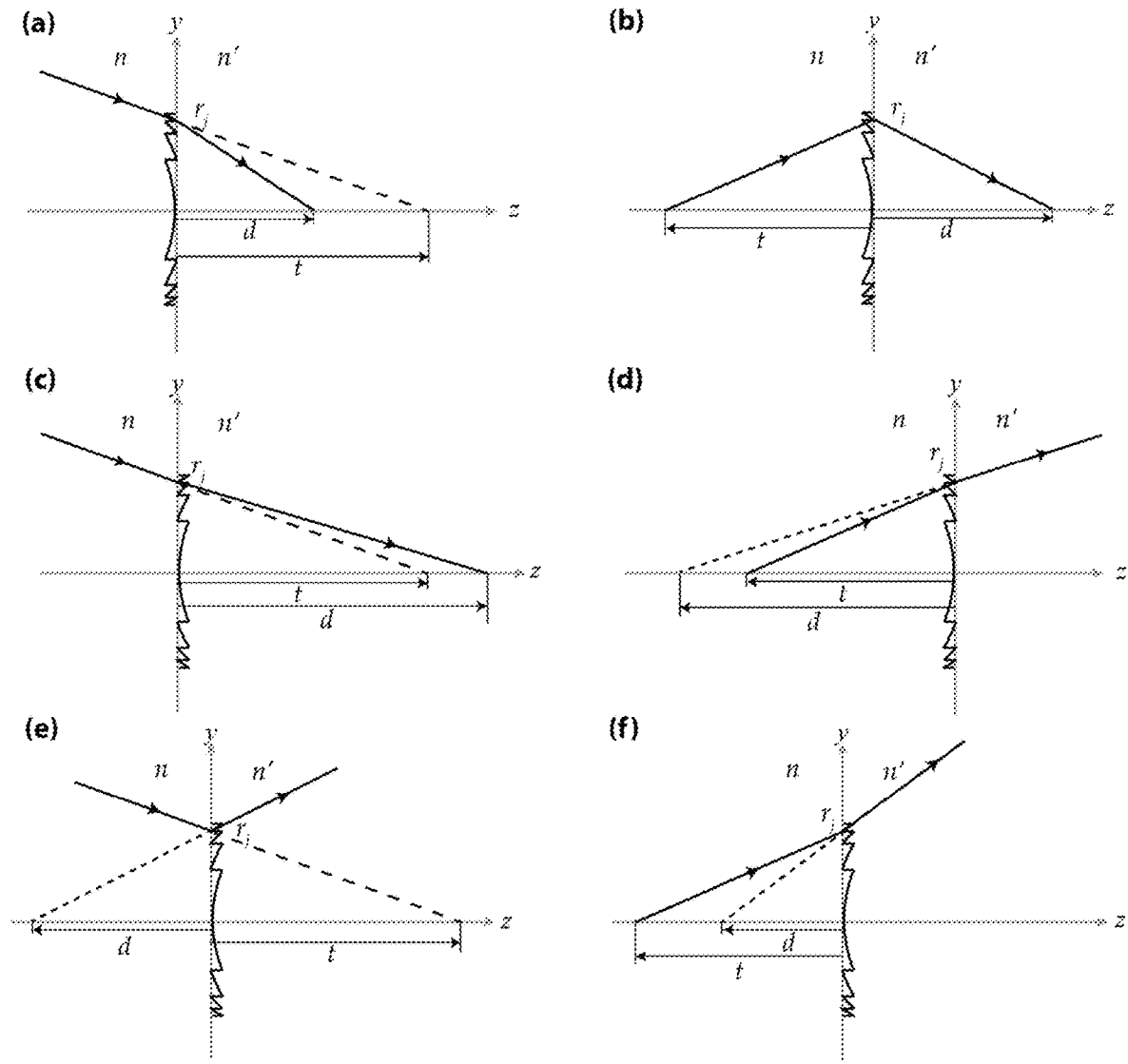
FIG. 15 presents six different cases of a diffractive surface on a flat substrate of a positive or negative power with a converging or diverging beam incidence.

FIG. 15 presents six different cases of a diffractive surface of a positive or negative power on a flat substrate with a converging or diverging beam incidence. t is the distance from the origin to the center of the incident beam. t>0 corresponds to a converging beam, and t<0 corresponds to a diverging beam. The six subplots in FIG. 15 are (a) a positive power (Φ>0) with a converging beam incidence (t>0), and d>0; (b) a positive power (Φ>0) with a diverging beam incidence (t<0), and d>0; (c) a negative power (Φ<0) with a converging beam incidence (t>0), and d>0; (d) a positive power (Φ>0) with a diverging beam incidence ($t<0$), and $d<0$; (e) a negative power ($\Phi<0$) with a converging beam incidence ($t>0$), and $d<0$; and (f) a negative power ($\Phi<0$) with a diverging beam incidence ($t<0$), and $d<0$.

Referring to FIG. 15(a), the OPL passing the Fresnel zone boundaries in this setup satisfies $$-nt+n'd+j\lambda_0 = n'\sqrt{d^2+r_j^2} - n\sqrt{t^2+r_j^2} \quad (40)$$

Square both sides of Eq.(40), and it can be rearranged as $$(n^2r_j^2+n'^2r_j^2+2nn'td+2ntj\lambda_0-2n'dj\lambda_0-j^2\lambda_0^2)^2 = 4n^2n'^2[t^2d^2+r_j^2(t^2+d^2)+r_j^4] \quad (41)$$

Assume that the diffractive surface semi-aperture $r_j$ of the j-th Fresnel zone is significantly smaller than both the incident beam radius and the first focal length of the diffractive surface, yet significantly larger than the design wavelength, i.e. $d \gg r_j \gg \lambda_0$ and $t \gg r_j \gg \lambda_0$. This assumption is valid for most applications of diffractive lenses, including the common use in ophthalmology. Therefore, the terms containing $\lambda_0^2$ and $r_j^4$ can be dropped, which yields $$r_j^2 = (2n^2n't^2dj\lambda_0 - 2nn'^2td^2j\lambda_0)/(n^2n'^2t^2+n^2n'^2d^2-n^3n'td-nn'^3td-n^3tj\lambda_0-nn'^2tj\lambda_0+n^2n'dj\lambda_0+n'^3dj\lambda_0) \quad (42)$$

The terms containing the factor $\lambda_0$ in the denominator are significantly smaller than the other terms in the denominator, hence can be dropped. Eq.(42) is further simplified into $$r_j^2 = \frac{2j\lambda_0 dt}{-nd+n't} = 2j\lambda_0 d' \quad (43)$$

where $$d' = d\zeta, \quad \zeta = \frac{t}{-nd+n't} \quad (44)$$

$\zeta$ is referred to as a Fresnel zone spacing factor hereafter, since it directly scales the spacing of Fresnel zones with respect to $\rho = r^2$.

The above Eq.(43) is linear to the zone number j, and it demonstrates that even with a converging beam incidence, as long as $d \gg r_j \gg \lambda_0$ and $t \gg r_j \gg \lambda_0$, the Fresnel zones are still of substantially equal area, even though this area is scaled, compared with that of plane wave incidence. For a SMUD lens, all the subzone areas are scaled proportionally, compared with those of plane wave incidence.

Correspondingly, with the updated d', the SMUD lens profile can still be summarized as Eq.(37). If periodically linear profile in each subzone is assumed, the SMUD lens profile is still Eq.(20).

A similar procedure can be analyzed for FIG. 15(b)-(f), and the results of the corresponding OPL equation at the Fresnel zone boundaries and the Fresnel zone spacing factor $\zeta$ are summarized in Table 4.

TABLE 4

| Lens Geometry | OPL equation & Fresnel zone spacing factor $\zeta$ |
|---|---|
| $\Phi > 0$, $t > 0, d > 0$ | $-nt + n'd + j\lambda_0 = n'\sqrt{d^2+r_j^2} - n\sqrt{t^2+r_j^2}$ <br> $\zeta = t/(-nd + n't)$ |
| $\Phi > 0$, $t < 0, d > 0$ | $-nt + n'd + j\lambda_0 = n'\sqrt{d^2+r_j^2} + n\sqrt{t^2+r_j^2}$ <br> $\zeta = t/(-nd + n't)$ |
| $\Phi > 0$, $t < 0, d < 0$ | $-nt + n'd + j\lambda_0 = -n'\sqrt{d^2+r_j^2} + n\sqrt{t^2+r_j^2}$ <br> $\zeta = t/(-nd + n't)$ |
| $\Phi < 0$, $t > 0, d > 0$ | $nt - n'd + j\lambda_0 = -n'\sqrt{d^2+r_j^2} + n\sqrt{t^2+r_j^2}$ <br> $\zeta = t/(nd - n't)$ |
| $\Phi < 0$, $t > 0, d < 0$ | $nt - n'd + j\lambda_0 = n'\sqrt{d^2+r_j^2} + n\sqrt{t^2+r_j^2}$ <br> $\zeta = t/(nd - n't)$ |
| $\Phi < 0$, $t < 0, d < 0$ | $nt - n'd + j\lambda_0 = n'\sqrt{d^2+r_j^2} - n\sqrt{t^2+r_j^2}$ <br> $\zeta = t/(nd - n't)$ |

Table 4 illustrates that although the OPL equations are different for different lens geometry, the Fresnel zone spacing factor is dependent on the sign of the lens power $\Phi$, and can be summarized as $$\zeta = \text{sgn}(\Phi)\frac{t}{-nd+n't} \quad (45)$$

Further, when $t \to \infty$, $\zeta \to \text{sgn}(\Phi)/n'$, $d' \to |d|/n'$, where sgn($\Phi$) is the sign function, and the above analysis reduces to the previous analysis for plane wave incidence.

The converging or diverging incident beam will introduce an extra factor in the transmission function. With paraxial approximation, the extra factor has the form of $$\exp\left(-\frac{i2\pi nt}{\lambda}\right)\exp\left(-\frac{i\pi nr^2}{\lambda t}\right)/|t|.$$

The $1/|t|$ factor comes from energy conservation, but it won't affect the energy distribution among different foci. The $$\exp\left(-\frac{i2\pi nt}{\lambda}\right)$$

phase factor is independent of $\rho$ and vanishes in $\eta_m$ after multiplying with its conjugate. Therefore, only the quadratic phase of $$\exp\left[-\frac{i\pi n(\lambda)r^2}{\lambda t}\right] = \exp\left[-\frac{i\pi n(\lambda)\rho}{\lambda t}\right]$$

has to be taken into account.

With converging or diverging incidence for a SMUD lens on a flat substrate, which is periodically linear in $\rho$ as described in Eq.(20) and Eq.(30), the Fourier coefficient is $$c_m = \gamma_1 e^{i\pi\gamma_1\left(m-\alpha\beta_1-\frac{n\lambda_0 d'}{\lambda t}\right)}\text{sinc}\left[\gamma_1\left(m-\alpha\beta_1-\frac{n\lambda_0 d'}{\lambda t}\right)\right] + (\gamma_2-\gamma_1) \quad (46)$$

$$e^{i\pi(\gamma_2+\gamma_1)\left(m-\alpha\beta_2-\frac{n\lambda_0 d'}{\lambda t}\right)}\text{sinc}\left[(\gamma_2-\gamma_1)\left(m-\alpha\beta_2-\frac{n\lambda_0 d'}{\lambda t}\right)\right] +$$

$$\ldots + (\gamma_g - \gamma_{g-1})e^{i\pi(\gamma_g+\gamma_{g-1})\left[m-\alpha\beta_g-\frac{n\lambda_0 d'}{\lambda t}\right]}\text{sin}$$

$$c\left[(\gamma_g - \gamma_{g-1})\left(m - \alpha\beta_g - \frac{n\lambda_0 d'}{\lambda t}\right)\right] + \ldots + (1 - \gamma_{G-1})$$

$$e^{i\pi(1+\gamma_{G-1})\left(m-\alpha\beta_G-\frac{n\lambda_0 d'}{\lambda t}\right)}\text{sinc}\left[(1-\gamma_{G-1})\left(m-\alpha\beta_G-\frac{n\lambda_0 d'}{\lambda t}\right)\right]$$

All the formulae of the Fourier coefficients $c_m$ and $\eta_m$ can be updated accordingly for SMUD lens designs with converging or diverging beam incidence.

Further, the substrate surface of a multifocal diffractive lens is not necessarily a flat surface. When the diffractive lens is formed on a curved substrate surface, a different Fresnel zone spacing factor has to be taken into account, and an extra phase in the transmission function will adjust the energy allocation among different foci.

In the following, plane wave incidence for a diffractive surface on a curved substrate is first analyzed. R is the radius of the substrate, R<0 corresponds to a convex substrate, since the lens material is to the left, and R>0 corresponds to a concave surface.

Figure 16:
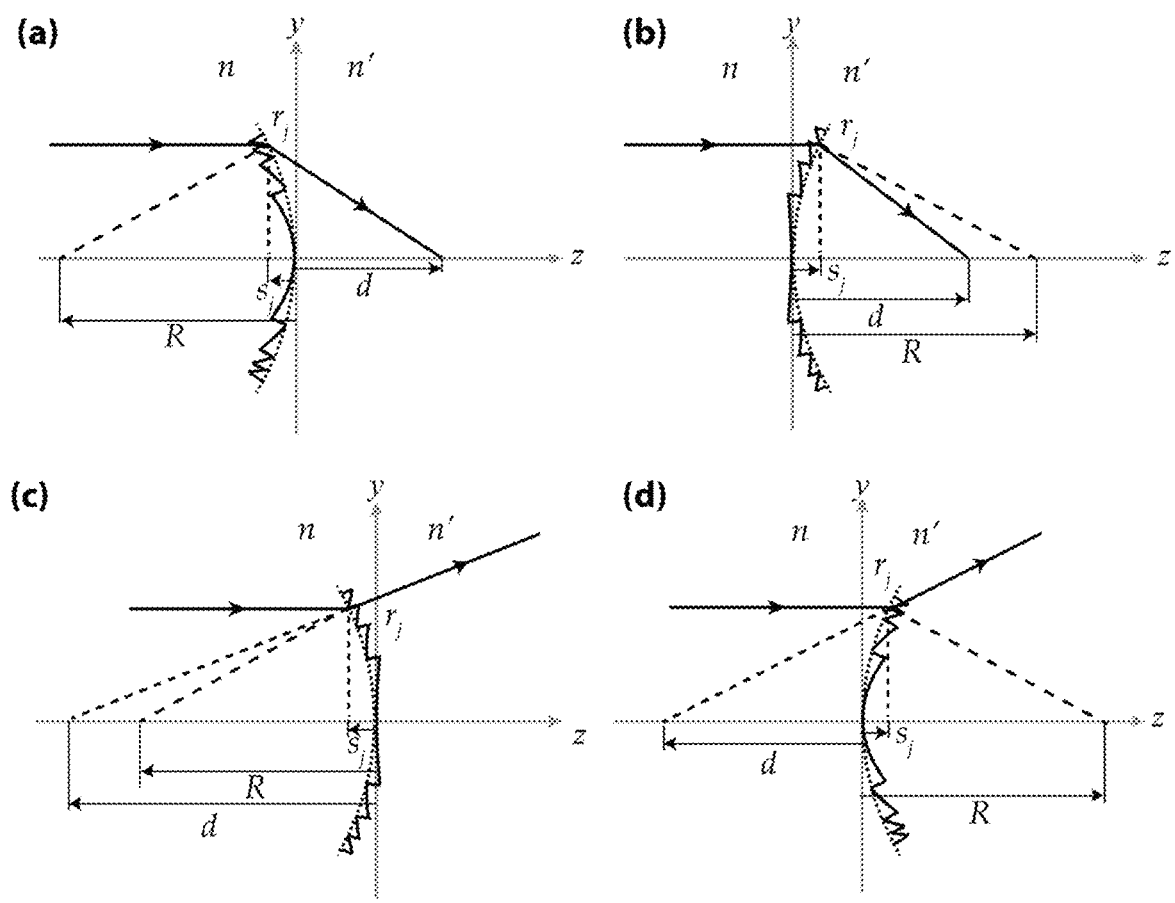
FIG. 16 presents four different cases of plane wave incidence to a positive or negative diffractive surface on a convexly or concavely curved substrate.

FIG. 16 presents four different cases of plane wave incidence with a positive or negative diffractive surface on a convexly or concavely curved substrate. The four subplots in FIG. 16 are (a) a positive power ($\Phi$>0, d>0) with a convex lens substrate (R<0); (b) a positive power ($\Phi$>0, d>0) with a concave lens substrate (R>0); (c) a negative power ($\Phi$<0, d<0) with convex lens substrate (R<0); and (d) a negative power ($\Phi$<0, d<0) with a concave lens substrate (R>0).

The OPL equation at the Fresnel zone boundaries in FIG. 16(a) is $$-ns_j + n'd + j\lambda_0 = n'\sqrt{(d-s_j)^2 + r_j^2} \quad (47)$$

where $s_j$ is the sag of the j-th zone, and $$s_j = \begin{cases} R - \sqrt{R^2 - r_j^2}, & R > 0 \\ R + \sqrt{R^2 - r_j^2}, & R < 0 \end{cases} \quad (48)$$

For many applications, including the common use in ophthalmology, $R \gg r_j \gg \lambda_0$. Keeping only the first two lower order terms of the Taylor series expansion of the square root in Eq.(48), the sag can be further approximated as $$s_j = \frac{r_j^2}{2R} \quad (49)$$

Square both side of Eq.(47), drop the small higher order terms containing $r_j^4$ and $\lambda_0^2$, and use Eq.(49) approximation to obtain $$r_j^2 = \frac{2j\lambda_0 dn'}{n'^2 - \frac{n'^2 d}{R} + \frac{nn'd}{R} + \frac{nj\lambda_0}{R}} = 2j\lambda_0 d' \quad (50)$$

Since $d \gg \lambda_0$, the term containing $\lambda_0$ in the denominator is small and can be dropped, Eq.(50) can be further simplified as $$r_j^2 = \frac{2j\lambda_0 d}{n' + (n-n')\frac{d}{R}} = 2j\lambda_0 d' \quad (51)$$

where $$d' = d\zeta, \quad \zeta = \frac{1}{n' + (n-n')\frac{d}{R}} \quad (52)$$

Similar procedures can be analyzed for FIG. (16)(b)-(d), and the results of the corresponding OPL equation at the Fresnel zone boundaries and the Fresnel zone spacing factor $\zeta$ are summarized in Table 5.

TABLE 5

| Lens Geometry | OPL equation & Fresnel zone spacing factor $\zeta$ |
| --- | --- |
| $\Phi > 0$ (d > 0) | $-ns_j + n'd + j\lambda_0 = n'\sqrt{(d-s_j)^2 + r_j^2}$<br>$\zeta = 1/[n' + (n-n')d/R]$ |
| $\Phi < 0$ (d < 0) | $ns_j - n'd + j\lambda_0 = n'\sqrt{(d-s_j)^2 + r_j^2}$<br>$\zeta = 1/[-n' - (n-n')d/R]$ |

Note that the form of the OPL equation and the spacing factor $\zeta$ formula are independent of the sign of R, but dependent on the sign of the lens power $\Phi$, and $\zeta$ can be summarized as $$\zeta = \text{sgn}(\Phi)\frac{1}{n' + (n-n')d/R} \quad (53)$$

When $R \to \infty$, the substrate becomes flat, which has been analyzed before, $\zeta \to \text{sgn}(\Phi)/n'$, and $d' \to |d|/n'$.

With paraxial approximation, the surface sag $s_j$ will cause an extra quadratic phase of $$\exp\left\{ik(\lambda)[n(\lambda) - n'(\lambda)]\frac{r^2}{2R}\right\} = \exp\left\{\frac{i\pi[n(\lambda) - n'(\lambda)]\rho}{\lambda R}\right\},$$

which has to be taken into account.

With plane wave incidence for a SMUD lens on a curved substrate, which is periodically linear in $\rho$ as described in Eq.(20) and Eq.(30), the Fourier coefficient is $$c_m = \gamma_1 e^{i\pi\gamma_1\left[m - \alpha\beta_1 + \frac{(n-n')\lambda_0 d'}{\lambda R}\right]} \text{sinc}\left\{\gamma_1\left[m - \alpha\beta_1 + \frac{(n-n')\lambda_0 d'}{\lambda R}\right]\right\} + \quad (54)$$

$$(\gamma_2 - \gamma_1)e^{i\pi(\gamma_2 + \gamma_1)\left[m - \alpha\beta_2 + \frac{(n-n')\lambda_0 d'}{\lambda R}\right]} \text{sin}$$

$$c\left\{(\gamma_2 - \gamma_1)\left[m - \alpha\beta_2 + \frac{(n-n')\lambda_0 d'}{\lambda R}\right]\right\} +$$

$$\ldots + (\gamma_g - \gamma_{g-1})e^{i\pi(\gamma_g + \gamma_{g-1})\left[m - \alpha\beta_g + \frac{(n-n')\lambda_0 d'}{\lambda R}\right]} \text{sin}$$

$$c\left\{(\gamma_g - \gamma_{g-1})\left[m - \alpha\beta_g + \frac{(n-n')\lambda_0 d'}{\lambda R}\right]\right\} +$$

$$\ldots + (1 - \gamma_{G-1})e^{i\pi(1+\gamma_{G-1})\left[m - \alpha\beta_G + \frac{(n-n')\lambda_0 d'}{\lambda R}\right]} \text{sin}$$

$$c\left\{(1 - \gamma_{G-1})\left[m - \alpha\beta_G - \frac{(n-n')\lambda_0 d'}{\lambda R}\right]\right\}$$

All the formulae of the Fourier coefficients $c_m$ and $\eta_m$ can be updated accordingly.

Figure 17:
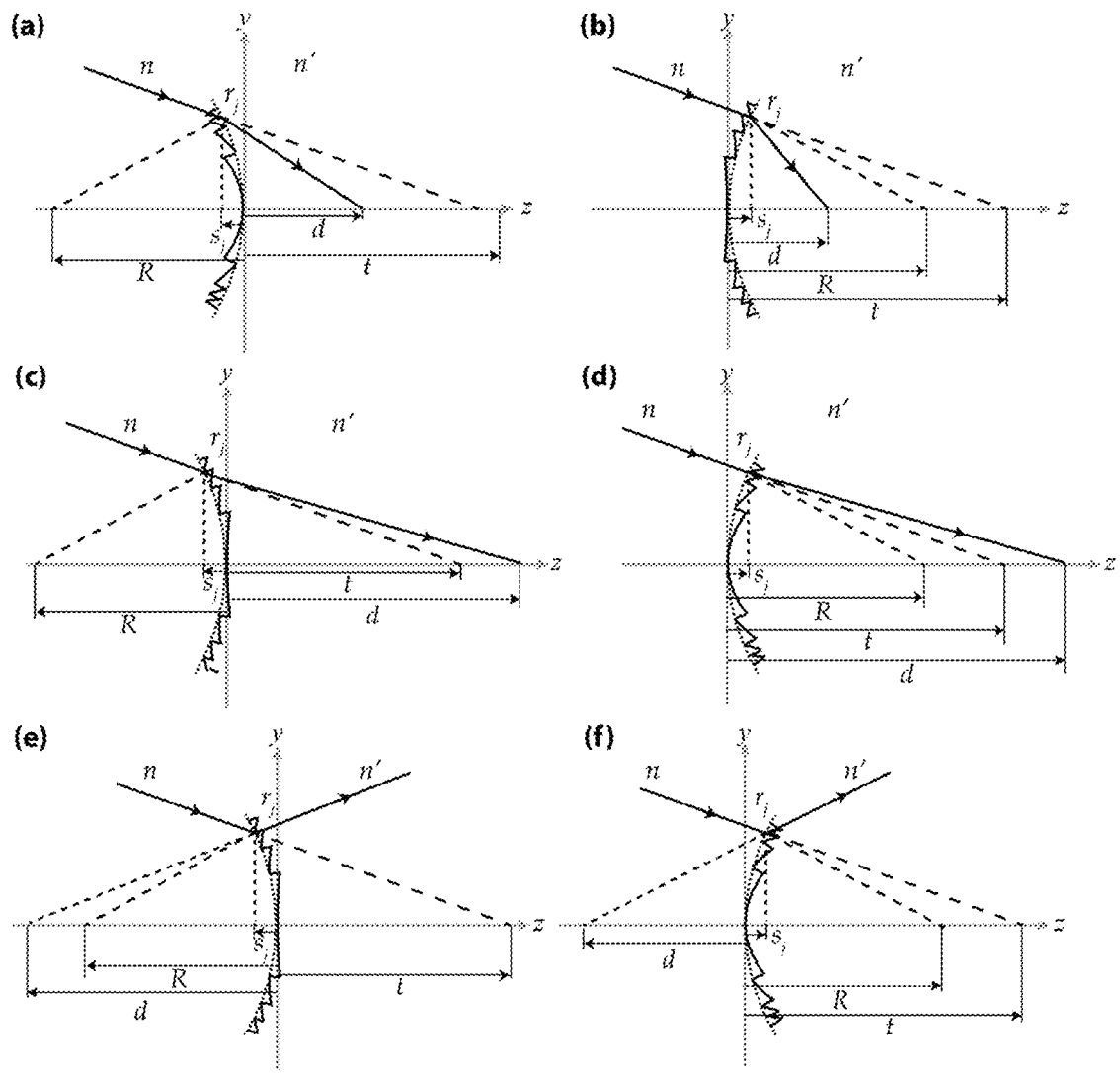
FIG. 17 presents six different cases of a converging incidence beam (t>0) with a positive or negative diffractive surface on a convexly or concavely curved substrate.

Next, the cases with converging beam incidence on a curved substrate are analyzed. FIG. 17 presents six different cases of a converging incidence beam (t>0) with a positive or negative diffractive surface on a convexly or concavely curved substrate. The six subplots in FIG. 17 are (a) converging beam incidence (t>0), positive power ($\Phi$>0), convex lens substrate (R<0), and d>0; (b) converging beam incidence (t>0), positive power ($\Phi$>0), concave lens substrate (R>0), and d>0; (c) converging beam incidence (t>0), negative power ($\Phi$<0), convex lens substrate (R<0), and d>0; (d)

converging beam incidence (t>0), negative power (Φ<0), concave lens substrate (R>0), and d>0; (e) converging beam incidence (t>0), negative power (Φ<0), convex lens substrate (R<0), and d<0; and (f) converging beam incidence (t>0), negative power (Φ<0), concave lens substrate (R>0), and d<0.

Referring to FIG. 17(a), a converging beam (t>0) is incident on a positive diffractive surface (Φ>0) on a convex substrate (R<0) with d>0. The OPL equation at the Fresnel boundaries is $$-nt + n'd + j\lambda_0 = n'\sqrt{(d-s_j)^2 + r_j^2} - n\sqrt{(t-s_j)^2 + r_j^2} \quad (55)$$

Square both sides of Eq.(55), and rearrange to obtain $$(2nn'td + 2ntj\lambda_0 - 2n'dj\lambda_0 - 2n^2ts_j - 2n'^2ds_j + n^2r_j^2 + n'^2r_j^2 + n^2s_j^2 + n'^2s_j^2 - j^2\lambda_0^2)^2 = 4n^2n'^2[(t^2 - 2ts_j + s_j^2 + r_j^2)(d^2 - 2ds_j + s_j^2 + r_j^2)] \quad (56)$$

With the assumption $d \gg r_j \gg \lambda_0$, $t \gg r_j \gg \lambda_0$, and $R \gg r_j \gg \lambda_0$, the higher order terms containing $\lambda_0^2$, $r_j^4$, $s_j^2$, and $s_j r_j^2$ can be dropped, and $$r_j^2 = (2n^2n't^2dj\lambda_0 - 2nn'^2td^2j\lambda_0) \Bigg/ \left( -\frac{n^2n'^2td^2}{R} + n^2n'^2d^2 - \frac{n^2n'^2t^2d}{R} + n^2n'^2t^2 + \frac{nn'^3td^2}{R} - n^3n'td - nn'^3td + \frac{n^3n't^2d}{R} + \frac{nn'^2td\,j\lambda_0}{R} - \frac{n'^3d^2j\lambda_0}{R} - n^3tj\lambda_0 + n'^3dj\lambda_0 + \frac{n^3t^2j\lambda_0}{R} - \frac{n^2n'tdj\lambda_0}{R} + n'n^2dj\lambda_0 - nn'^2tj\lambda_0 \right) \quad (57)$$

The terms containing $\lambda_0$ in the denominator are small compared with other terms in the denominator, and can be further dropped, so Eq.(57) can be simplified as $$r_j^2 = \frac{2j\lambda_0 dt}{n't - nd + \frac{td}{R}(n - n')} = 2j\lambda_0 d' \quad (58)$$

where $$d' = d\zeta, \quad \zeta = \frac{t}{n't - nd + \frac{td}{R}(n - n')} \quad (59)$$

Figure 18:
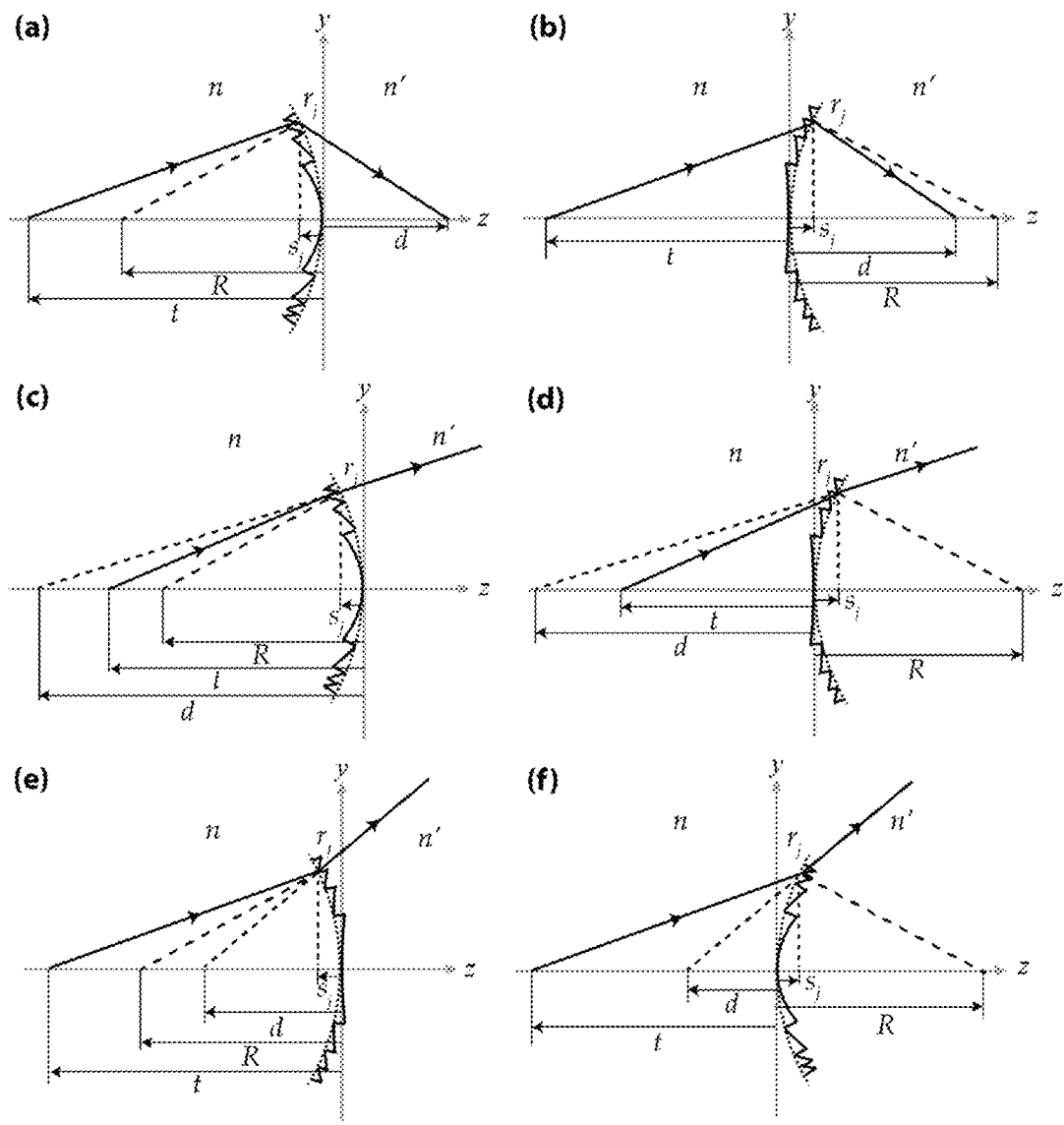
FIG. 18 presents six different cases of a diverging incidence beam (t<0) with a positive or negative diffractive surface on a convexly or concavely curved substrate.

FIG. 18 presents six different cases of a diverging incidence beam (t<0) with a positive or negative diffractive surface on a convexly or concavely curved substrate. The six subplots in FIG. 18 are (a) diverging beam incidence (t<0), positive power (Φ>0), convex lens substrate (R<0), and d>0; (b) diverging beam incidence (t<0), positive power (Φ>0), concave lens substrate (R>0), and d>0; (c) diverging beam incidence (t<0), positive power (Φ>0), convex lens substrate (R<0), and d<0; (d) diverging beam incidence (t<0), positive power (Φ>0), concave lens substrate (R>0), and d<0; (e) diverging beam incidence (t<0), negative power (Φ<0), convex lens substrate (R<0), and d<0; and (f) diverging beam incidence (t<0), negative power (Φ<0), concave lens substrate (R>0), and d<0.

Similar analysis can be done for FIG. 17(b)-(f) of converging beam incidence and FIG. 18(a)-(f) of diverging beam incidence, and the results of the corresponding OPL equation at the Fresnel zone boundaries and the Fresnel zone spacing factor ζ are summarized in Table 6.

TABLE 6

| Lens Geometry | OPL equation & Fresnel zone spacing factor ζ |
| --- | --- |
| Φ > 0, t > 0, d > 0 | $-nt + n'd + j\lambda_0 = n'\sqrt{(d-s_j)^2 + r_j^2} - n\sqrt{(t-s_j)^2 + r_j^2}$ <br> $\zeta = t/[n't - nd + (n - n')td/R]$ |
| Φ > 0, t < 0, d > 0 | $-nt + n'd + j\lambda_0 = n'\sqrt{(d-s_j)^2 + r_j^2} + n\sqrt{(t-s_j)^2 + r_j^2}$ <br> $\zeta = t/[n't - nd + (n - n')td/R]$ |
| Φ > 0, t < 0, d < 0 | $-nt + n'd + j\lambda_0 = -n'\sqrt{(d-s_j)^2 + r_j^2} + n\sqrt{(t-s_j)^2 + r_j^2}$ <br> $\zeta = t/[n't - nd + (n - n')td/R]$ |
| Φ < 0, t > 0, d > 0 | $nt - n'd + j\lambda_0 = -n'\sqrt{(d-s_j)^2 + r_j^2} + n\sqrt{(t-s_j)^2 + r_j^2}$ <br> $\zeta = t/[-n't + nd - (n - n')td/R]$ |
| Φ < 0, t > 0, d < 0 | $nt - n'd + j\lambda_0 = n'\sqrt{(d-s_j)^2 + r_j^2} + n\sqrt{(t-s_j)^2 + r_j^2}$ <br> $\zeta = t/[-n't + nd - (n - n')td/R]$ |
| Φ < 0, t < 0, d < 0 | $nt - n'd + j\lambda_0 = n'\sqrt{(d-s_j)^2 + r_j^2} - n\sqrt{(t-s_j)^2 + r_j^2}$ <br> $\zeta = t/[-n't + nd - (n - n')td/R]$ |

Note that the form of the OPL equation and the spacing factor ζ formula are independent of the sign of R, but dependent on the sign of Φ. For Φ>0, even though the original OPL equations at the zone boundaries are different for different lens geometries, after simplification, the Fresnel zone spacing factors ζ are the same for three different (t, d) pairs. The same conclusion also applies to the case of Φ<0. The Fresnel zone spacing factor ζ can be summarized as $$\zeta = \text{sgn}(\Phi) \frac{t}{n't - nd + (n - n')td/R} \quad (60)$$

Further, when t→∞, incident beam becomes plane wave, and Table 6 reduces to Table 5.

When R→∞, the substrate becomes flat, and Table 6 reduces to Table 4.

When t→∞, and R→∞, d'=|d|/n', and the above analysis reduces to the previous analysis for a flat substrate with plane wave incidence.

Similar to Eq.(43), (51), and (58), the Fresnel zone boundaries of the configurations drawn in FIG. 15~18, are all linear to the zone number j, and it demonstrates that for a diffractive surface on a curved substrate with converging or diverging beam incidence, as long as $d \gg r_j \gg \lambda_0$, $t \gg r_j \gg \lambda_0$, and $R \gg r_j \gg \lambda_0$, the optimal Fresnel zones are still of substantially equal area, even though this area is scaled by a Fresnel zone spacing factor ζ. The substantially equal areas of the Fresnel zones are defined with respect to radius squared $r^2$, and they correspond to projected areas in a plane perpendicular to the optical axis of the diffractive lens. For a SMUD lens, the projected areas of all the subzones are scaled proportionally.

With converging or diverging beam incidence for a SMUD lens on a curved substrate, which is periodically linear in ρ as described in Eq.(20) and Eq.(30), the Fourier coefficient is $$c_m = \gamma_1 e^{i\pi\gamma_1\left[m-\alpha\beta_1-\frac{n\lambda_0 d'}{\lambda t}+\frac{(n-n')\lambda_0 d'}{\lambda R}\right]}$$

$$\text{sinc}\left\{\gamma_1\left[m-\alpha\beta_1-\frac{n\lambda_0 d'}{\lambda t}+\frac{(n-n')\lambda_0 d'}{\lambda R}\right]\right\}+$$

$$(\gamma_2-\gamma_1)e^{i\pi(\gamma_2+\gamma_1)\left[m-\alpha\beta_2-\frac{n\lambda_0 d'}{\lambda t}+\frac{(n-n')\lambda_0 d'}{\lambda R}\right]}\text{sinc}$$

$$\left\{(\gamma_2-\gamma_1)\left[m-\alpha\beta_2-\frac{n\lambda_0 d'}{\lambda t}+\frac{(n-n')\lambda_0 d'}{\lambda R}\right]\right\}+$$

$$\ldots+(\gamma_g-\gamma_{g-1})e^{i\pi(\gamma_g+\gamma_{g-1})\left[m-\alpha\beta_g-\frac{n\lambda_0 d'}{\lambda t}+\frac{(n-n')\lambda_0 d'}{\lambda R}\right]}\sin$$

$$c\left\{(\gamma_g-\gamma_{g-1})\left[m-\alpha\beta_g-\frac{n\lambda_0 d'}{\lambda t}+\frac{(n-n')\lambda_0 d'}{\lambda R}\right]\right\}+$$

$$\ldots+(1-\gamma_{G-1})e^{i\pi(1+\gamma_{G-1})\left[m-\alpha\beta_G-\frac{n\lambda_0 d'}{\lambda t}+\frac{(n-n')\lambda_0 d'}{\lambda R}\right]}\sin$$

$$c\left\{(1-\gamma_{G-1})\left[m-\alpha\beta_G-\frac{n\lambda_0 d'}{\lambda t}+\frac{(n-n')\lambda_0 d'}{\lambda R}\right]\right\}$$

(61)

All the formulae of the Fourier coefficients $c_m$ and $\eta_m$ can be updated accordingly for SMUD lenses.

Therefore, a curved substrate and/or a converging or diverging beam incidence will demand changes in the Fresnel zone boundaries. They also demand the subzone boundaries and corresponding lens profile to change proportionally. The diffraction efficiency analysis also have to be adjusted by taking into account of the incidence beam shape and the substrate curvature.

In the mathematical framework of this invention, apodization essentially means monotonically decreasing the phase step factor β with respect to r or ρ. For a SMUD lens, apodization means decreasing the phase step factors $β_s$ of corresponding subzones with respect to r or ρ. An apodization factor can be absorbed into $β_s$ as $$\beta_s = \beta_{s0} f_{apodize} \quad (62)$$

where $β_{s0}$ is the phase step factor of a subzone if there is no apodization. The apodization factor decreases across part of or the entire diffractive surface.

The basic concept of apodization can be understood by referring to FIG. 3. In the range of β∈[0, 1], as β approaches 0, the zeroth order diffraction efficiency approaches 1, while that of all other orders approaches 0.

It is important to point out that many functions that monotonically decrease with radius r can be used as an apodization factor, and all these apodization factors can be applied to SMUD lenses, if preferred. For example, here one novel form of the apodization factor is proposed:

$$f_{apodize1} = \cos^{e_2}\left[\frac{\pi}{2}\left(\frac{r-r_{in}}{r_{out}-r_{in}}\right)^{e_1}\right], r_{in} \le r < r_{out} \quad (63)$$

when $e_2=1$, Eq.(63) reduces to $$f_{apodize2} = \cos\left[\frac{\pi}{2}\left(\frac{r-r_{in}}{r_{out}-r_{in}}\right)^{e_1}\right], r_{in} \le r < r_{out} \quad (64)$$

If $e_2>1$, $f_{apodize1}$ always decreases faster than $f_{apodize2}$, and if $0<e_2b<1$, $f_{apodize1}$ always decreases slower than $f_{apodize2}$.

The larger $e_1$ is, the slower the apodization factor drops near the center, and the more steeply it declines when r reaches the edge of the apodization region.

Furthermore, the apodization factor could also be a piecewise function, as long as it's monotonically decreasing from the center to the periphery within the apodized region.

Figure 19:
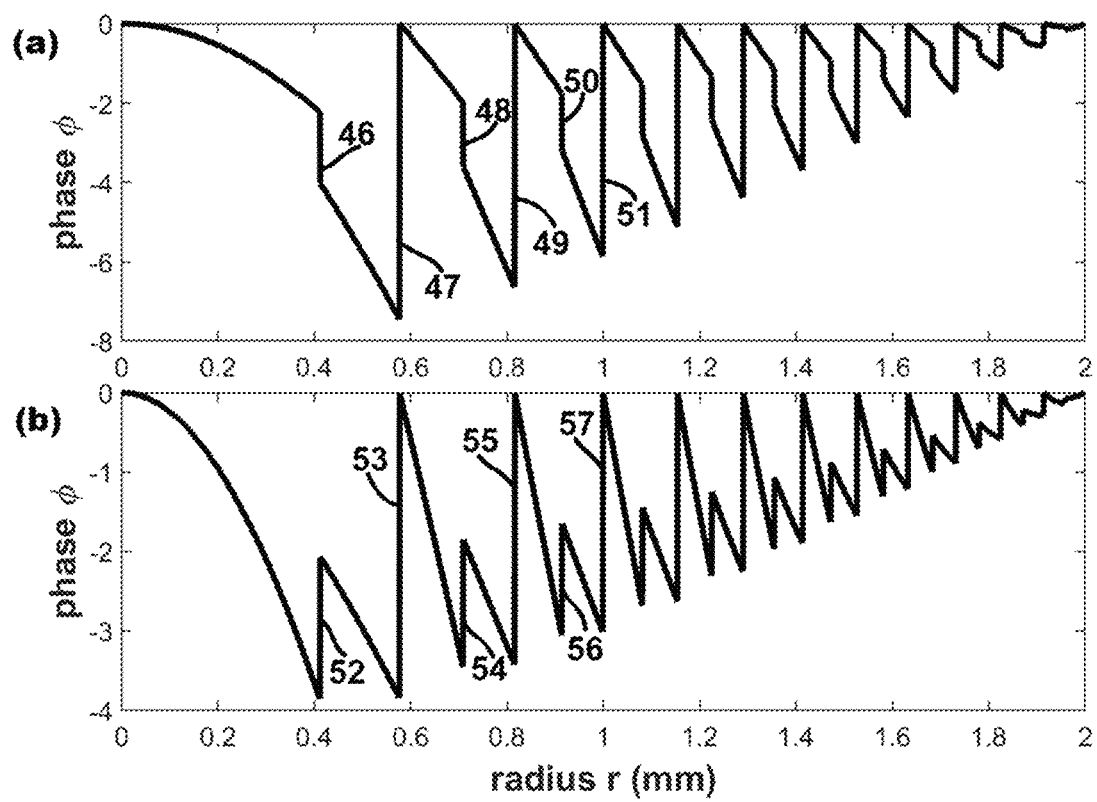
FIG. 19 presents two representative SMUD lens phase profiles with apodization.

Exemplary apodization profiles of two-subzone SMUD lenses are shown in FIG. 19. FIG. 19 presents two phase profiles with the apodization factor in the form of Eq.(64) for Design #3 (19a) and #4 (19b). $r_{in}=0$ mm, $r_{out}=2$ mm, $e_1=1$. In FIG. 19(a), 46, 48, and 50, in order, are the phase steps of between the first type subzone and the second type subzone of the first three Fresnel zones. In FIG. 19(a), 47, 49, and 51, in order, are the phase steps between a Fresnel zone and its adjacent Fresnel zone. With apodization, 46, 48, 50 and similar phase steps between the corresponding subzones, i.e. between a first type subzone and a second type subzone of all the apodized Fresnel zones, form a group of phase steps gradually decreasing from the center to the periphery of the diffractive surface. Similarly, 47, 49, 51 and other phase steps between a Fresnel zone and its corresponding adjacent Fresnel zone form another group of phase steps also gradually decreasing from the center to the periphery of the diffractive surface.

In the same manner, in FIG. 19(b), 52, 54, 56 and similar phase steps between the corresponding subzones, i.e. between a first type subzone and a second type subzone of all the apodized Fresnel zones, form a group of phase steps gradually decreasing from the center to the periphery of the diffractive surface. In FIG. 19(b), 53, 55, 57 and other phase steps between a Fresnel zone and its corresponding adjacent Fresnel zone form another group of phase steps also gradually decreasing from the center to the periphery of the diffractive surface.

A varying β across different Fresnel zones violates the periodicity in ρ, hence the transmission function of the lens could no longer be expanded as a Fourier series. However, Eq.(10) and Eq.(11) can still be used to estimate the local diffraction efficiency based on the local spatial frequency, as if the local periodicity of the region under investigation extends to a large scale.

Figure 20:
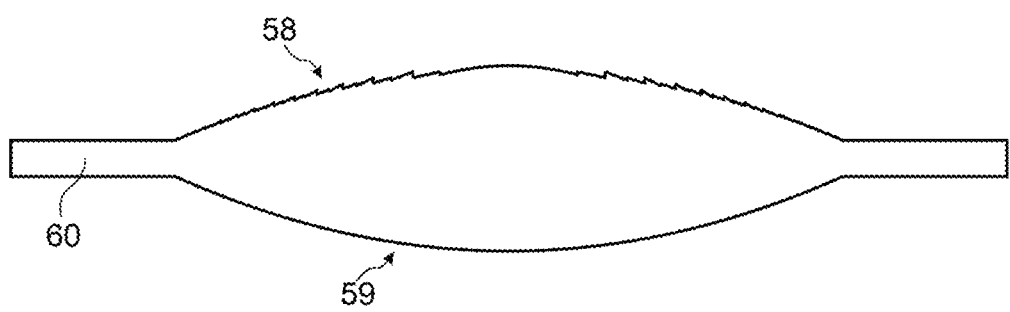
FIG. 20 presents a cross-sectional view of one embodiment of the lens in this invention, which combines an apodized diffractive surface and a refractive surface.

Further, FIG. 20 presents a cross-sectional view of one embodiment of the lens in this invention, in which a diffractive surface is combined with a refractive surface on the other side of the lens. In FIG. 20, a subzonal diffractive surface 58 is from Design #4 with an apodization factor of FIG. 19 (b) based on Eq.(64). A refractive surface 59 is on the other side of the lens; a haptics structure 60 is used to hold the lens in a desired position.

For a SMUD lens, the ophthalmic astigmatism can be corrected by combining a toric surface with a fixed cylinder power and a subzonal multifocal diffractive surface, or the astigmatism correction can be achieved by two separate lenses, one is a toric lens, and the other is a SMUD lens. In one preferred embodiment of the refractive surface 59 in FIG. 20 is a toric surface with a cylinder power to correct ophthalmic astigmatism.

Even though in the preferred embodiment of the lens, the lens surface 58 is a subzonal multifocal diffractive surface, and the lens surface 59 is a refractive surface, it is possible that the surface 59 is also a diffractive surface, or even a subzonal multifocal diffractive surface. For some applications, the surface 59 could also be a reflective surface.

All publications, patents and patent applications referred to herein are incorporated by reference in their entirety to the same extent as if each individual publication, patent or patent application was specifically and individually indicated to be incorporated by reference in its entirety in the present application.

While this invention has been described in detail with particular reference to certain preferred embodiments, it is to be understood that the invention is not limited to the disclosed embodiments. Modification and variation of this invention may be made without departing from the scope of the invention.

What is claimed is:

1. A multifocal diffractive lens comprising:
a lens having a first surface,
wherein said first surface is subzonal multifocal diffractive,
wherein at least a portion of said first surface of said lens comprises a plurality of concentric annular zones from a center to a periphery of said lens along radius r, wherein each said zone is a Fresnel zone,
wherein each said zone has a projected area in a plane perpendicular to an optical axis of said lens,
wherein said projected areas of said zones are of equal areas,
wherein each said zone is divided into at least two subzones with at least one division ratio within each zone,
wherein each of said at least two subzones has a phase profile and a projected area in said plane perpendicular to said optical axis of said lens,
wherein said phase profile of each of said at least two subzones is independent of all other subzones within the same zone,
wherein said at least one division ratio is the same across all said zones, so that a repetitive pattern is formed with respect to radius squared $r^2$ of said portion of said first surface of said lens,
wherein a phase step is formed at the edge of each subzone.

2. The lens of claim 1, wherein said phase profile is a thickness profile, wherein said thickness profile of said subzone changes with radius r from an inner edge of said subzone to an outer edge of said subzone.

3. The lens of claim 2, wherein said thickness profile is formed by a lathe or a mold.

4. The lens of claim 2, wherein said thickness profile is formed by optically matching two materials with different refractive indices.

5. The lens of claim 1, wherein said phase profile is a refractive index profile, wherein said refractive index profile of said subzone changes with radius r from an inner edge of said subzone to an outer edge of said subzone.

6. The lens of claim 5, wherein said refractive index profile is formed by altering the refractive index of a portion of a material comprising said lens by laser micromachining, doping or ion exchange.

7. The lens of claim 1, wherein said phase profile is characterized by a phase step factor.

8. The lens of claim 1, wherein the projected area of at least one subzone is different from the projected areas of all the other subzones within the same zone.

9. The lens of claim 1, wherein said subzonal multifocal diffractive first surface is formed on a substrate with a curvature.

10. The lens of claim 9, wherein said projected area of each zone is adjusted by a Fresnel zone spacing factor applied to all zones, based on the convergence or divergence of a light beam incident on said lens, and said curvature of said substrate.

11. The lens of claim 1, wherein said at least one division ratio and the phase profile of each subzone are individually independent.

12. The lens of claim 1, further comprising a second surface, wherein said second surface is a refractive surface.

13. The lens of claim 12, wherein said second refractive surface is of a toric shape with a cylinder power.

14. The lens of claim 1, wherein the phase steps of corresponding subzones of each zone monotonically decrease from the center to the periphery of at least a portion of said subzonal multifocal diffractive first surface.

15. The lens of claim 1, wherein said lens is an intraocular lens.

16. The lens of claim 1, wherein said lens is a contact lens.

17. The lens of claim 1, wherein said lens is an intracorneal lens.

18. The lens of claim 1, wherein said lens is a trifocal lens.

19. The lens of claim 1, wherein said lens is a quadrifocal lens.

* * * * *